(12) United States Patent
Davis

(10) Patent No.: US 11,766,196 B1
(45) Date of Patent: Sep. 26, 2023

(54) DEVICES, SYSTEMS, AND METHODS FOR HANDLING NOISE IN NON-INVASIVE BIOLOGICAL INTERROGATION TECHNIQUES

(71) Applicant: Brigham Young University, Provo, UT (US)

(72) Inventor: Robert C. Davis, Provo, UT (US)

(73) Assignee: Brigham Young University, Provo, UT (US)

( * ) Notice: Subject to any disclaimer, the term of this patent is extended or adjusted under 35 U.S.C. 154(b) by 361 days.

(21) Appl. No.: 17/206,831

(22) Filed: Mar. 19, 2021

Related U.S. Application Data

(60) Provisional application No. 62/991,764, filed on Mar. 19, 2020.

(51) Int. Cl.
| | |
|---|---|
| *A61B 5/145* | (2006.01) |
| *A61B 5/00* | (2006.01) |
| *A61B 5/1455* | (2006.01) |
| *A61B 5/053* | (2021.01) |

(52) U.S. Cl.
CPC ........ *A61B 5/14532* (2013.01); *A61B 5/0022* (2013.01); *A61B 5/053* (2013.01); *A61B 5/14535* (2013.01); *A61B 5/14546* (2013.01); *A61B 5/14552* (2013.01); *A61B 5/4875* (2013.01); *A61B 5/681* (2013.01); *A61B 5/7203* (2013.01); *A61B 5/742* (2013.01)

(58) Field of Classification Search
CPC ... A61B 5/14532; A61B 5/0022; A61B 5/053; A61B 5/14535; A61B 5/14546; A61B 5/14552; A61B 5/4875; A61B 5/681; A61B 5/7203; A61B 5/742
See application file for complete search history.

(56) References Cited

U.S. PATENT DOCUMENTS

| | | | |
|---|---|---|---|
| 2010/0130883 A1* | 5/2010 | Carpenter | A61B 5/053 600/547 |
| 2016/0198961 A1* | 7/2016 | Homyk | A61B 5/681 600/476 |

\* cited by examiner

*Primary Examiner* — Eric F Winakur
*Assistant Examiner* — Abid A Mustansir
(74) *Attorney, Agent, or Firm* — Miller IP Law, LLC

(57) ABSTRACT

Devices, systems, and methods for eliminating noise in non-invasive biological interrogation techniques may be described herein. A method may include taking a first set of measurements over a time period. The first set of measurements may be indicated by an electronic signal. The first set of measurements may correspond to a physiological characteristic of a subject. A change in the physiological characteristic of the subject may correspond to a change in a blood constituent of the subject. The method may include: taking a second set of measurements over the time period; correlating the first and second sets of measurements, wherein the correlating removes noise from the electronic signal; sectioning out the electronic signal; calculating an amplitude difference between two or more sections of the electronic signal; and determining a change in the amount of the blood constituent based on the difference.

20 Claims, 12 Drawing Sheets

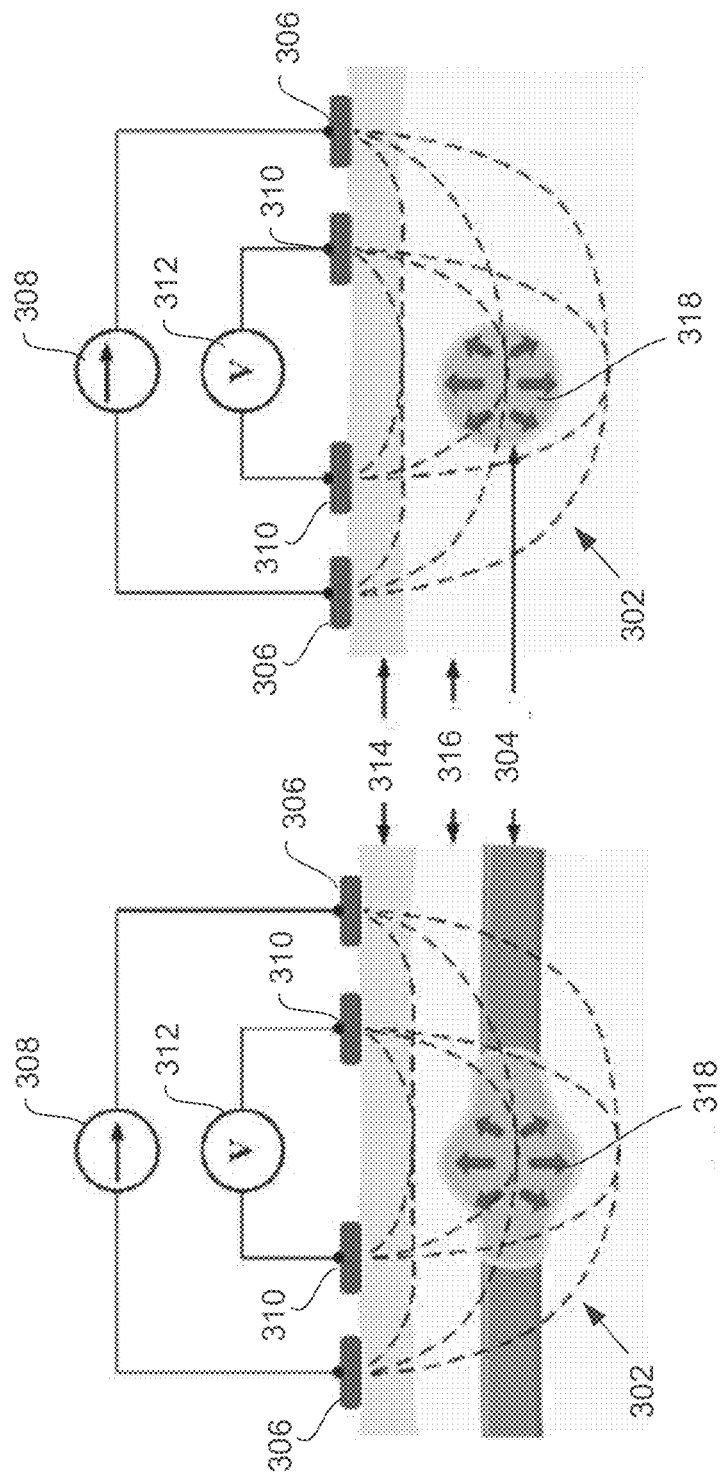

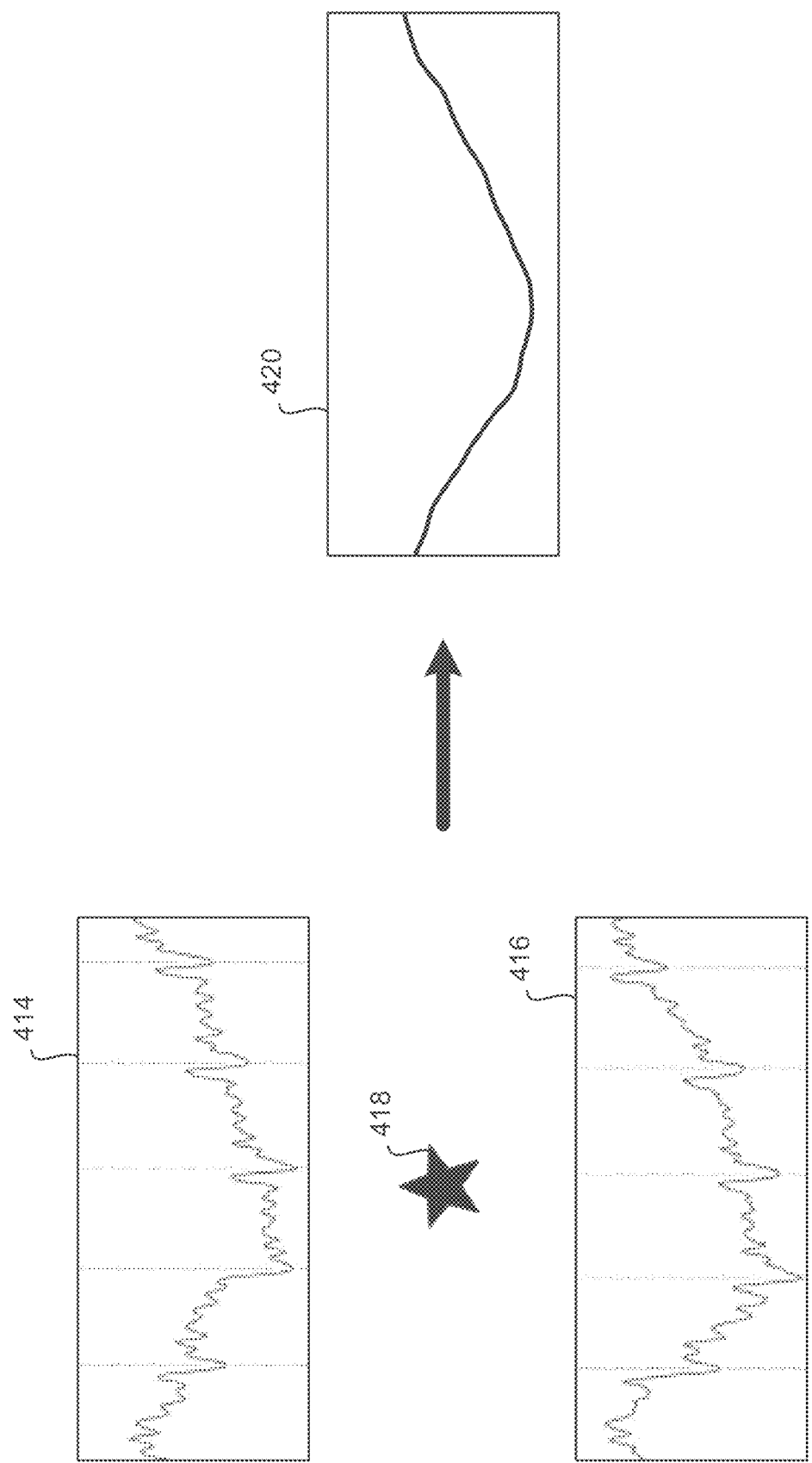

DEVICES, SYSTEMS, AND METHODS FOR HANDLING NOISE IN NON-INVASIVE BIOLOGICAL INTERROGATION TECHNIQUES

CROSS-REFERENCES

This application claims priority to U.S. Provisional Patent Application No. 62/991,764 entitled "DEVICES, SYSTEMS, AND METHODS FOR HANDLING NOISE IN NON-INVASIVE BIOLOGICAL INTERROGATION TECHNIQUES" and filed on Mar. 19, 2020. The entire contents of the provisional application are incorporated herein by reference.

BACKGROUND

Measurement of various biological and/or physiological functions of an organism can provide information relevant to a health status of the organism. Often, particularly regarding animal organisms such as humans, collecting such measurement data may be challenging or impossible without harming the organism. For example, in humans, measuring various characteristics of blood may require puncturing the skin, a vein, and/or an artery, withdrawing the blood, and performing tests on the blood in vitro. Such invasive measurement techniques may allow for identification of blood constituents such as blood glucose, hematocrit levels, hormone levels, and so forth. Some techniques have been developed to non-invasively measure some biological and/or physiological characteristics that were previously measured invasively. Non-invasive measurement may include using electrical, impedance, and/or optical devices to interrogate the characteristic of interest.

BRIEF DESCRIPTION OF DRAWINGS

The present description will be understood more fully when viewed in conjunction with the accompanying drawings of various examples of handling noise in non-invasive biological interrogation techniques. The description is not meant to limit the handling noise in non-invasive biological interrogation techniques to the specific examples. Rather, the specific examples depicted and described are provided for explanation and understanding of handling noise in non-invasive biological interrogation techniques. Throughout the description, the drawings may be referred to as drawings, figures, and/or FIGs.

FIG. 3A illustrates impedance paths aligned parallel to an artery, according to an embodiment.

FIG. 3B illustrates impedance paths aligned perpendicular to an artery, according to an embodiment.

FIG. 4B is a pictorial representation of a correlation of two different types of measurements, according to an embodiment.

DETAILED DESCRIPTION

Figure 1A:
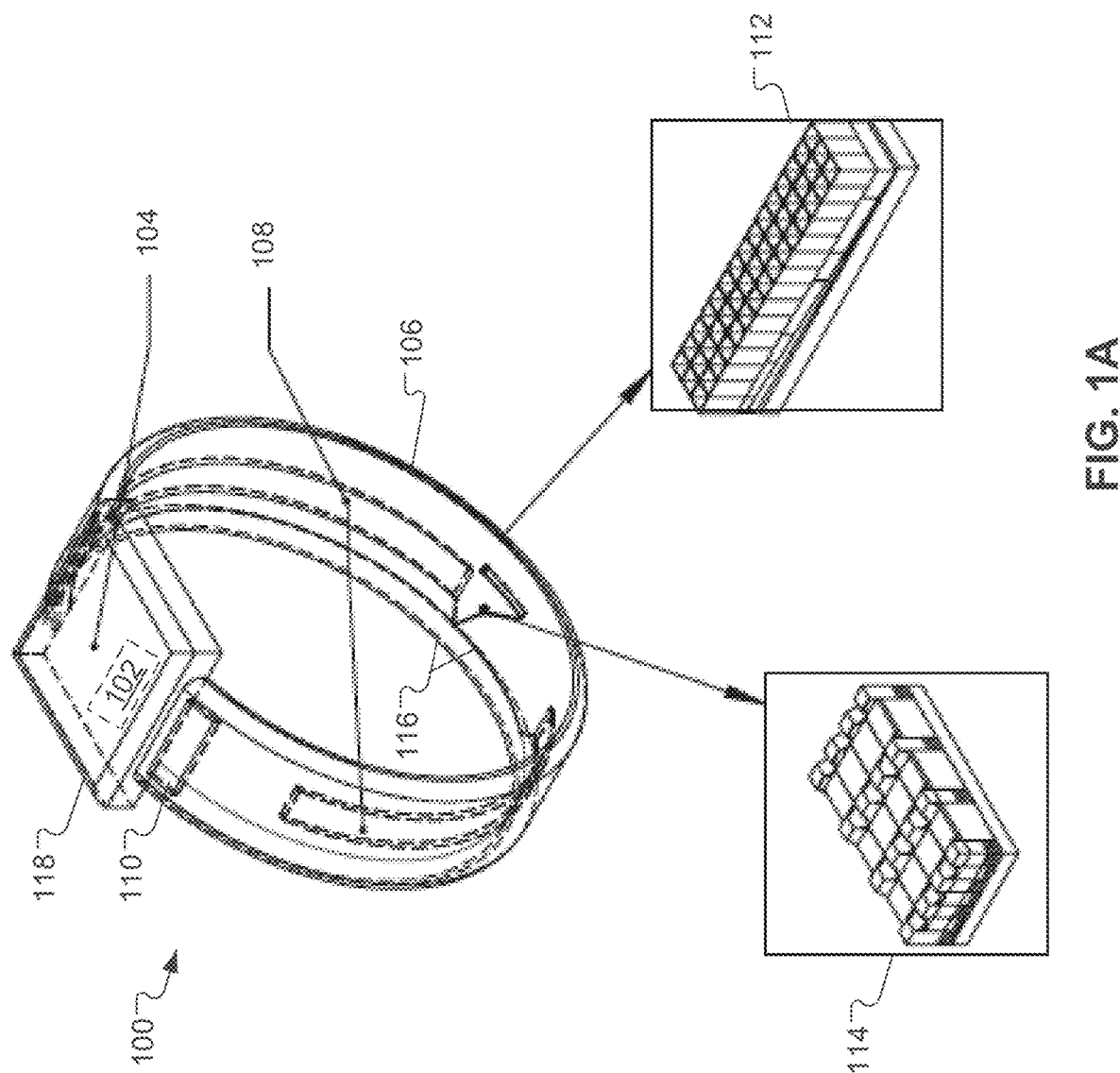
FIG. 1A illustrates a wearable device with integrated sensors, according to an embodiment.

Devices, systems, and methods for handling noise in non-invasive biological interrogation techniques as disclosed herein will become better understood through a review of the following detailed description in conjunction with the figures. The detailed description and figures provide merely examples of the various embodiments of handling noise in non-invasive biological interrogation techniques. Many variations are contemplated for different applications and design considerations; however, for the sake of brevity and clarity, all the contemplated variations may not be individually described in the following detailed description. Those skilled in the art will understand how the disclosed examples may be varied, modified, and altered and not depart in substance from the scope of the examples described herein.

Throughout the following detailed description, examples of handling noise in non-invasive biological interrogation techniques are provided. Related elements in the examples may be identical, similar, or dissimilar in different examples. For the sake of brevity and clarity, related elements may not be redundantly explained in multiple examples. Instead, the use of same, similar, and/or related element names and/or reference characters may cue the reader that an element with a given name and/or associated reference character may be similar to another related element with the same, similar, and/or related element name and/or reference character in an example explained elsewhere herein. Elements specific to a given example may be described regarding that particular example. A person having ordinary skill in the art will understand that a given element need not be the same and/or similar to the specific portrayal of a related element in any given figure or example to share features of the related element.

As used herein, "same" means sharing all features and "similar" means sharing a substantial number of features or sharing materially important features even if a substantial number of features are not shared. As used herein, "may" should be interpreted in a permissive sense and should not be interpreted in an indefinite sense. Additionally, use of "is" regarding examples, elements, and/or features should be interpreted to be definite only regarding a specific example and should not be interpreted as definite regarding every similar embodiment. Furthermore, references to "the disclosure" and/or "this disclosure" refer to the entirety of the writings of this document and the entirety of the accompanying illustrations, which extends to all the writings of each section of this document, including the Title, Background, Brief description of the Drawings, Detailed Description, Claims, Abstract, and any other document and/or resource incorporated herein by reference.

As used herein regarding a list, "and" forms a group inclusive of all the listed elements. For example, an embodiment described as including A, B, C, and D is an embodiment that includes A, includes B, includes C, and also includes D. As used herein regarding a list, "or" forms a list of elements, any of which may be included. For example, an embodiment described as including A, B, C, or D is an embodiment that includes any of the elements A, B, C, and D. Unless otherwise stated, an embodiment including a list of alternatively-inclusive elements does not preclude other embodiments that include various combinations of some or all of the alternatively-inclusive elements. An embodiment described using a list of alternatively-inclusive elements includes at least one element of the listed elements. However, an embodiment described using a list of alternatively-inclusive elements does not preclude another embodiment that includes all of the listed elements. And, an embodiment described using a list of alternatively-inclusive elements does not preclude another embodiment that includes a combination of some of the listed elements. As used herein regarding a list, "and/or" forms a list of elements inclusive alone or in any combination. For example, an embodiment described as including A, B, C, and/or D is an embodiment that may include: A alone; A and B; A, B and C; B, C, and D; C and D; A, B, C, and D; and or any other combination thereof. The bounds of an "and/or" list are defined by the complete set of combinations and permutations for the list. The bounds of "or" elements or "and/or" elements does not exclude the inclusion of other elements not listed therein and may include combinations or mixtures of elements from various embodiments and example provided herein.

Where multiples of a particular element are shown in a FIG., and where it is clear that the element is duplicated throughout the FIG., only one label may be provided for the element, despite multiple instances of the element being present in the FIG. Accordingly, other instances in the FIG. of the element having identical or similar structure and/or function may not have been redundantly labeled. A person having ordinary skill in the art will recognize based on the disclosure herein redundant and/or duplicated elements of the same FIG. Despite this, redundant labeling may be included where helpful in clarifying the structure of the depicted example embodiments.

A conventional interrogation technique may be invasive. For example, measurement of blood glucose levels, hormone levels, hematocrit levels, and so forth may be measured by taking a blood sample from a subject and performing various in vitro tests to determine the quantities of the various elements of interest. Some non-invasive techniques have been employed to determine levels and characteristics of blood constituents. For example, blood alcohol content may be measured using a breathalyzer. Blood oxygenation may be measured using lights emitting specific wavelengths and optical sensors that measure scattering of the wavelengths of interest through a subject's body part.

However, conventional non-invasive interrogation techniques fall short in accuracy and may, therefore, be unreliable. Impacts to the accuracy of non-invasive interrogation techniques may generally be referred to as "noise." Conventional techniques for enhancing a signal-to-noise ratio of a non-invasive measurement may not sufficiently isolate an element of interest or may cause loss of information related to other elements of interest.

Devices, systems, and methods for handling noise in non-invasive biological interrogation techniques may include non-invasively and approximately contemporaneously measuring a physiological characteristic of a subject using at least two different types of sensors and correlating the measurements by the two different types of sensors. For example, the physiological characteristic may include a volumetric change in a vein or artery as the subject's heartbeats. The sensors may include an optical sensor and light source, a bioimpedance sensor, a pressure sensor, and so forth. Noise from one of the sensors may be different than noise from the other sensor. However, some of the noise may be due to an element of interest. The noise due to the element of interest may be present in both measurements. correlation of the measurements may reduce and/or eliminate noise unrelated to the element of interest while retaining information about the element of interest.

FIG. 1A illustrates a wearable device 100 with integrated sensors 112 and/or 114, according to an embodiment. Some of the features in FIG. 1A are the same as or similar to some of the features in the other FIGs. described herein as noted by same and/or similar reference characters, unless expressly described otherwise. Additionally, reference may be made to features shown in any of the other FIGs. described herein and not shown in FIG. 1A. In one embodiment, the wearable device 100 may be configured to take physiological measurements from a subject of one or more physiological characteristics of the subject. The wearable device 100 may include a housing 118 and a band 106 that are configured or shaped to attach to a body of the subject. In one embodiment, the wearable device 100 may include a wrist-worn device that may be configured to attach to a wrist or arm of the subject. In another embodiment, the wearable device 100 may be attached to a head of the subject using a headband, to a chest of the subject using a chest band, to an ankle of the subject using an ankle band, or otherwise attached to the body of the subject using, for example, a sweatband, bandage, band, watch, bracelet, ring, adherent, or other attachments and connections.

The wearable device 100 may include a processing device 102, a display device 104, the band 106, a power source 108, a processing unit 110, a first sensor 112, and/or a second sensor 114. In one embodiment, the processing device 102 and the display device 104 may be integrated into the housing 118 of the wearable device 100. In another embodiment, the power source 108, the processing unit 110, the first sensor 112, and/or the second sensor 114 may be integrated into the band 106 of the wearable device 100. In one embodiment, the band 106 may include a cavity that the power source 108, the processing unit 110, the first sensor 112, and/or the second sensor 114 may be stored in. In another embodiment, the band 106 may be formed or molded over the power source 108, the processing unit 110, the first sensor 112, and/or the second sensor 114. In another embodiment, the power source 108, the first sensor 112, and/or the second sensor 114 may be connected to the processing unit 110 and/or the processing device 102 by one or more electrical trace(s) or circuit(s) 116 (such as flexible circuit boards).

The processing device 102 and/or the processing unit 110 may provide an output based on an input. In an embodiment, the processing device 102 and/or the processing unit 110 may include a central processing unit, a graphics processing unit, a vision processing unit, a tensor processing unit, a neural processing unit, a physics processing unit, a digital signal processor, an image signal processor, a synergistic processing element, a field-programmable gate array, a sound chip, a microprocessor, a multi-core processor, and so forth.

In one embodiment, the first sensor 112 may include a miniaturized spectrometer. In another embodiment, the second sensor 114 may include an impedance sensor. In another embodiment, the first sensor 112 and/or the second sensor may include a photoplethysmography (PPG) sensor, a temperature sensor, a viscosity sensor, an ultrasonic sensor, a humidity sensor, a heart rate sensor, a dietary intake sensor, an electrocardiogram (EKG) sensor, a galvanic skin response sensor, a pulse oximeter, an optical sensor, a velocity liquid level sensor, a pressure sensor, a displacement (position) sensor, a vibration sensor, a chemical sensor, a force radiation sensor, a pH-value sensor, a strain sensor, an acoustic field sensor, an electric field sensor, a photoconductive sensor, a photodiode sensor, a through-beam sensor, a retro-reflective sensor, a diffuse reflection sensor, and so forth. In another embodiment, the wearable device 100 may include other sensors integrated or attached to the band 106 or the housing 118. In another embodiment, the wearable device 100 may be communicatively coupled to the wearable device 100, such as sensors of other devices or third-party devices. The first sensor 112 and/or the second sensor 114 may be configured to take measurements from a subject non-invasively, such as by electrical and/or optical interrogation, and so forth.

The first sensor 112 and/or the second sensor 114 may be coupled to the processing unit 110. The processing unit 110 may be configured to manage or control the first sensor 112, the second sensor 114, and/or the power source 108. In one embodiment, the processing unit 110 may control a frequency or rate over time that the first sensor 112 and/or the second sensor 114 take measurements, a wavelength or optical frequency at which the first sensor 112 and/or the second sensor 114 take measurements, a power consumption level of the first sensor 112 and/or the second sensor 114, a sleep mode of the first sensor 112 and/or the second sensor 114 and so forth. In another embodiment, the processing unit 110 may control or adjust measurements taken by the first sensor 112 and/or the second sensor 114 take measurements to remove noise, reduce a signal to noise ratio, dynamically adjust the number of measurements taken over time, and so forth.

In another embodiment, the power source 108 may be coupled to the processing unit 110. The power source 108 may include a battery, a solar panel, a kinetic energy device, a heat converter power device, a wireless power receiver, and so forth. The processing unit 110 may be configured to transfer power from the power source 108 to the processing device 102, the display 104, the first sensor 112, the second sensor 114, and/or other devices or units of the wearable device 100. In one embodiment, the processing unit 110 may be configured to regulate an amount of power provided from the power source 108 to the processing device 102, the display 104, the first sensor 112, the second sensor 114, and/or other devices or units of the wearable device 100. In another embodiment, the wearable device 100 may include a power receiver to receive power to recharge the power source 108. For example, the power receiver may include a wireless power coil, a universal serial bus (USB) connector, a thunderbolt connector, a mini USB connector, a micro USB connector, a USB-C connector, and so forth. The power receiver may be coupled to the processing unit 110, the processing device 102, the power source 108, and so forth.

In one embodiment, the processing unit 110 may be configured to regulate an amount of power provided from the power receiver to the power source 108. In another embodiment, the processing unit 110 may include a power management unit configured to control battery management, voltage regulation, charging functions, direct current (DC) to DC conversion, voltage scaling, power conversion, dynamic frequency scaling, pulse-frequency modulation (PFM), pulse-width modulation (PWM), amplification, and so forth. In another embodiment, the processing unit 110 may include a communication device configured to send and/or receive data via a cellular communication channel, a wireless communication channel, a Bluetooth® communication channel, a radio communication channel, a WiFi® communication channel, a USB communication channel, a fiber-optic communication channel, and so forth.

The processing device 102 may include a processing device, a data storage device, a communication device, a graphics processor, and so forth. In one embodiment, the processing device 102 may be coupled to the processing unit 110, the power source 108, the first sensor 112, and/or the second sensor 114. In one embodiment, the processing device 102 may be configured to receive measurement data from the processing unit 110, the first sensor 112, and/or the second sensor 114. In one embodiment, the processing device 102 may be configured to process the measurement data and display information associated with the measurement data at the display 104. In another embodiment, the processing device 102 may be configured to communicate the measurement data to another device. In one embodiment, the other device may process the measurement data and provide information associated with the measurement data to the subject or another individual. In another embodiment, the other device may process the measurement data and provide results, analytic information, instructions, and/or notifications to the processing device 102 to provide to the subject. The wearable device 100 may communicate information associated with the measurement data or information related to the measurement data to a subject via the display 104, a buzzer, a vibrator, a speaker, a microphone, and so forth.

In another embodiment, the wearable device 100 may be part of a system connected to other devices. For example, the wearable device 100 may be configured to send and/or receive data with another device. In one embodiment, the wearable device 100 may be configured to receive data from another measurement device, aggregate the received data with measurement data from the first sensor 112 and/or the second sensor 114, analyze the aggregated data, and provide information or notifications associated with the analyzed data.

Figure 1B:
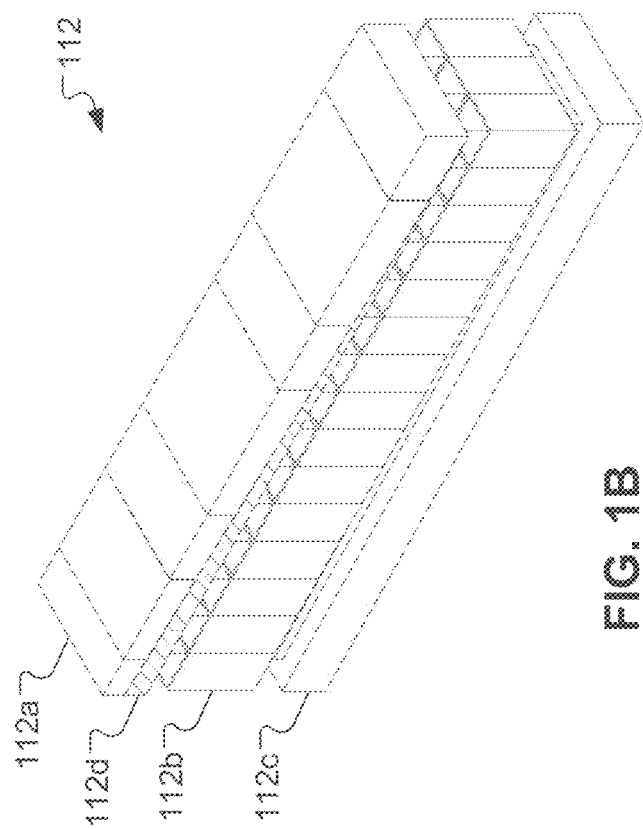
FIG. 1B illustrates a side perspective exploded view of the first sensor described regarding FIG. 1A, according to an embodiment.

FIG. 1B illustrates a side perspective exploded view of the first sensor 112, according to an embodiment. Some of the features in FIG. 1B may be the same as or similar to some of the features in the other FIGs. described herein as noted by same and/or similar reference characters, unless expressly described otherwise. Additionally, reference may be made to features shown in any of the other FIGs. described herein and not shown in FIG. 1B. In one embodiment, the first sensor 112 may include a miniaturized spectrometer. The first sensor 112 may include a filter 112a, a collimator 112b, and an optical sensor 112c. In one embodiment, the filter 112a may include an optical filter, such as a variable filter, a linear variable filter, an absorptive filter, a dichroic filter, a monochromatic filter, an infrared filter, an ultraviolet filter, a neutral density filter, a long-pass filter, a band-pass filter, a short-pass filter, a guided-mode resonance filter, a metal mesh filter, a polarizer filter, an arc welding filter, a wedge filter, and so forth. In another embodiment, the filter may include a Fabry-Perot Etalon filter.

The filter 112a may include a linear variable filter. The linear variable filter may allow for selecting which wavelengths strike the optical sensor 112c at a specific position on the optical sensor 112c. This may allow a processor such as the processing unit 110 and/or the processing device 102 to, in turn, distinguish the relative intensities of wavelengths reflected from a tissue to determine which wavelengths are most strongly reflected from the tissue relative to an initial intensity of those wavelengths as emitted from a light source. The processor may determine, based on the reflected wavelengths, one or more parameters, constituents, and/or conditions of the tissue. For example, light having a first wavelength may strike a first region of the optical sensor 112c corresponding to a first region of the filter 112a. The first wavelength may correspond to a constituent of a subject's blood. The optical sensor 112c may communicate the intensity of the first wavelength to the processor. The processor may process the first wavelength based on an emitted intensity of the wavelength, an expected attenuation of the wavelength, and/or other attenuation factors to determine an amount of the constituent in the subject's blood. Different constituents of the subject's blood may transmit and/or reflect wavelengths of light at different intensities. The filter 112a may pass different wavelengths to different positions on the optical sensor 112c. The optical sensor 112c may pass the intensities of the corresponding wavelengths to the processor, and the processor may determine an amount of a blood constituent based on the relative intensities of the wavelengths.

In an embodiment, the filter 112a may include an absorptive filter. The absorptive filter may be formed to have distinct cutoff edges between regions of the absorptive filter corresponding to different wavelength ranges. Furthermore, the absorptive filter may be manufactured of a durable and/or flexible material. In an embodiment, the filter 112a may include a dichroic filter, which may also be referred to as an interference filter. The dichroic filter may be variable. The dichroic filter may allow for a very precise selection of wavelengths to be passed through the filter 112a. For example, the dichroic filter may have a transmission profile with a narrow peak, such as a full-width half max (FWHM) wavelength range of 50 nm, 40 nm, 30 nm, 25 nm, 20 nm, 10 nm, 5 nm, and/or 1 nm. The dichroic filter may be implemented in embodiments where the filter 112a is incorporated into a sensor for measuring sensitive phenomena. The sensitive phenomena may include various physiological parameters, conditions, and/or constituents for which small-percentage changes, such as less than or equal to a 50 percent change, results in dramatically different outcomes. For example, the sensitive phenomenon may include a blood acidity level. A healthy blood acidity may include a pH of 7.4. A blood pH less than or equal to 6.8 or greater than or equal to 7.8 may result in irreversible cell damage. In another example, the sensitive phenomenon may include bone density.

In an embodiment, the filter 112a may include a grism. In an embodiment, the filter 112a may include a prism coupled to a diffraction grating. The grism or the coupled prism and diffraction grating may be referred to as the grism. In various embodiments, the prism may include a dispersion prism and/or a prismatic sheet, such as a Fresnel prism. In various embodiments, the diffraction grating may include a ruled grating, a holographic grating, a transmission grating, a reflective grating, a blazed holographic grating, a concave grating, an aberration-corrected concave grating, a constant deviation monochromator concave grating, a Rowland type concave grating, a blazed holographic concave grating, a sinusoidal holographic grating, a sinusoidal ruled grating, a pulse compression grating, and so forth. In an embodiment, the diffraction grating may include a volume phase holographic (VPH) grating. In an embodiment, the diffraction grating may diffract impinging light along one dimension or along two dimensions.

In one embodiment, the collimator 112b may include a device that restricts beam(s) of particles or waves passing into the first sensor 112, such as light in visible and/or non-visible wavelengths, to specific directions of motion, angles, or ranges of angles to become more aligned in a specific direction as the beam(s) travels through the first sensor 112. The collimator 112b may restrict a spatial cross-section of the beam(s). In an embodiment, the collimator 112b may restrict the beam(s) along one dimension and/or along two dimensions.

The collimator 112b may be formed in one or more of a variety of ways. In various embodiments, the collimator 112b may be formed of one or more microtubes. In an embodiment, the collimator 112b may include a plurality of microtubes, where a microtube of the plurality of microtubes is defined by one or more walls encircling a through-channel. A microtube of the plurality of microtubes may have a width ranging from 10 microns to 150 microns, and/or a height ranging from 30 microns to 500 microns. For example, the microtube may have a height equal to less than a thickness of 4 pages of printer paper, and a width equal to less than a thickness of 1 page of printer paper. The microtubes may be prepared separately and joined together, such as by a binder, or the microtubes may be prepared together. For example, the walls of the microtubes may be formed of CNTs. A catalyst layer may be patterned on a substrate forming an impression of the plurality of microtubes, and the CNTs may be grown on the catalyst layer, forming the walls encircling the through-channels to form the microtubes. In another embodiment, the collimator 112b may include a volume of material through which pores and/or apertures are formed. The volume of material may, for example, include a photoresist material. The pores and/or apertures may be etched through the photoresist material, such as by photolithography or plasma etching.

The collimator 112b may be positioned against the filter 112a and/or the optical sensor. For example, the collimator 112b may be disposed between the filter 112a and the optical sensor 112c, or the filter 112a may be disposed between the collimator 112b and the optical sensor 112c. In an embodiment, a wall forming a microtube of the collimator 112b may be aligned normal to a surface of the filter 112a and/or a surface of the optical sensor 112c. In an embodiment, the light may pass through the filter 112a and the collimator 112b may allow the light within a range of normal incidence passing from the filter 112a to impinge on the optical sensor 112c. In another embodiment, the collimator 112b may allow light to impinge on the filter 112a within a range of normal incidence. In yet another embodiment, the collimator wall may be aligned at a non-normal angle relative to the surface of the filter 112a and/or the surface of the optical sensor 112c. The angle may correspond to an angle of separated light leaving the filter 112a.

The optical sensor 112c may be operable to convert light rays into electronic signals. For example, the optical sensor 112c may measure a physical quantity of light such as intensity and translate the measurement into a form that is readable by the processor such as an amount of current corresponding directly to the intensity of the light. In an embodiment, the optical sensor 112c may include a semiconductor. The semiconductor may have one or more bandgaps corresponding to a wavelength and/or wavelength range. The semiconductor may be arranged into an array, such as an array of pixels, corresponding to regions of the filter 112a such as a first region, a second region, and so forth.

The optical sensor 112c may include a segment such as a pixel. In an embodiment, the optical sensor 112c may include a plurality of the segment arrange in an array, such as an array of pixels. The sensor segment may be aligned with a region of the filter 112a. The segment may have an identifier such that the processor may associate the segment with the region of the filter. The identifier may enable the processor to determine a wavelength of light detected by the segment of the optical sensor 112c. For example, in one embodiment, the optical sensor may include a first sensor segment aligned with a first filter region, a second sensor segment aligned with a second filter region, and so forth. The first sensor segment may be identified by the processor as detecting a wavelength and/or range of wavelengths that may correspond to a passband of the first filter region. For example, wavelengths ranging from 400 nm to 449 nm may pass unfiltered through the first filter region. The unfiltered light may strike the first sensor segment, and the first sensor segment may, in response generate an electrical signal that may be transmitted to the processor. The processor may identify the electrical signal as being transmitted by the first sensor segment and may identify that signals transmitted by the first sensor segment may be generated by light having a wavelength ranging from 400 nm to 449 nm.

In one embodiment, the filter 112a, the collimator 112b, and the optical sensor 112c may be stacked together to form the first sensor 112. In one example, the filter 112a, the collimator 112b, and the optical sensor 112c may be integrated to form an integrated sensor body. In another example, the filter 112a, the collimator 112b, and the optical sensor 112c may be interconnected together. In one example, the filter 112a, the collimator 112b, and the optical sensor 112c may be stacked vertically on top of each other. In another embodiment, the filter 112a may be wedge-shaped where one end of the filter 112a has a relatively thick end that tapers to a thinner edge. In one embodiment, the collimator 112b and the optical sensor 112c may have relatively flat top surfaces and/or bottom surfaces. When the filter is a wedge shape, a filling material 112d may be attached or affixed to the collimator 112b and/or the optical sensor 112c so that the filter 112a may rest or attach flush or level to the collimator 112b and/or the optical sensor 112c. In one example, the filling material 112d may include an optically transparent material (such as clear glass or a clear plastic), an optically translucent material (such as polyurethane, colored or frosted glass, colored or frosted plastic, and so forth), or other material that does not interfere with defined wavelengths of light. In another example, the filling materials 112d may be attached or affixed to the collimator 112b and/or the optical sensor 112c by an adhesive, by welding, by friction, by a pressure fit, and so forth.

Figure 1C:
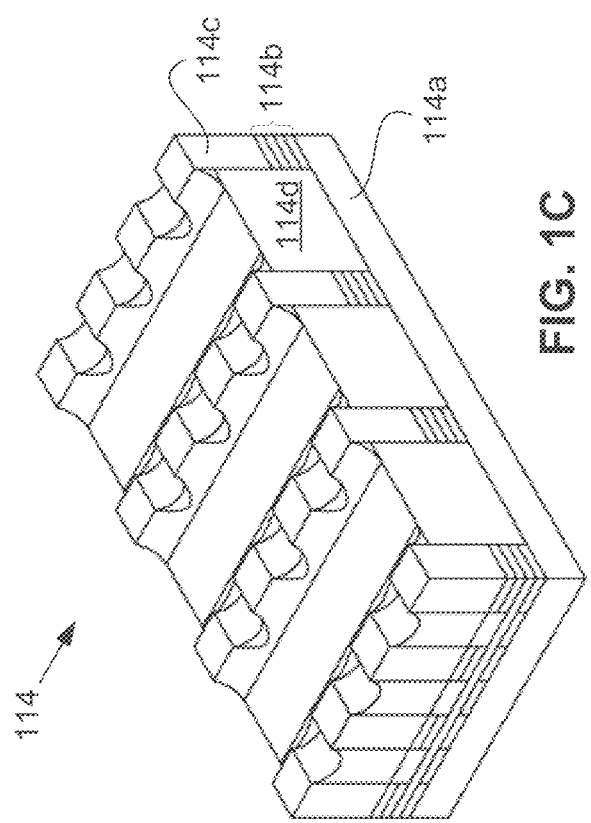
FIG. 1C illustrates a perspective view of the second sensor described regarding FIG. 1A, according to an embodiment.

FIG. 1C illustrates a perspective view of the second sensor 114, according to an embodiment. Some of the features in FIG. 1C may be the same as or similar to some of the features in the other FIGs. described herein as noted by same and/or similar reference characters, unless expressly described otherwise. Additionally, reference may be made to features shown in any of the other FIGs. described herein and not shown in FIG. 1C. The second sensor 114 may include an impedance sensor. The impedance sensor may include a substrate 114a which may provide structural support for one or more microstructures. The microstructures may include various intermediate layers 114b, a microelectrode 114c, and/or an interstitial filler 114d. In an embodiment, the impedance sensor may include the substrate 114a, one or more of the intermediate layers 114b, the microelectrode 114c, and/or the interstitial filler 114d. The impedance sensor may include a plurality of microelectrodes 114c.

The substrate 114a may provide a base support structure for deposition, growth, and/or etching of the microstructures. The substrate 114a may provide a support structure for integrating the second sensor 114 into the wearable device 100. In one embodiment, the substrate 114a may include a silicon and/or a tungsten wafer. In another embodiment, the substrate 114a may include glass, such as a glass fiber-reinforced resin. In an embodiment, the substrate 114a may be formed of a flexible material such as polyimide. The substrate 114a may include one or more conductors, such as an electrical trace or a through-surface via. The conductors may electrically couple the microelectrodes 114c to electronics external to the second sensor 114, such as a processor.

The various intermediate layers 114b may include a conductive layer, one or more insulating layers, and/or a catalyst layer. The conductive layer may electrically couple the microelectrode 114c to the substrate 114a conductor. The catalyst layer may catalyze growth of the microelectrode 114c. In an embodiment, the intermediate layers 114b may include one or more ceramic insulating layers, such as alumina, which may be rendered conductive by a preparation process of the impedance sensor.

The microelectrode 114c may include a bundle of nanotubes. The bundle may be infiltrated with a bolstering material, where bolster may refer to a property of a material that increases resistance against an applied force of the material and/or another material with which the material is incorporated. Accordingly, the bolstering material may increase the rigidity of the bundle relative to similarly structured bundles not including the bolstering material. The bolstering material may reduce the brittleness of the bundle relative to similarly structured bundles not including the bolstering material. For example, the nanotubes may include Carbon Nanotubes (CNTs) grown on an iron catalyst. The bolstering material may include carbon, a metal, and/or a conductive polymer. In one embodiment, the microelectrode 114c may include CNTs infiltrated with carbon. In another embodiment, the microelectrode 114c may include CNTs infiltrated with a conductive polymer. In another embodiment, the microelectrode 114c may include a polymer coated with a conductive film. The conductive film may include a thin film. The thin film may include metal and/or carbon. In an embodiment, the polymer may be formed into a pillar.

In one embodiment, the interstitial filler 114d may be positioned between rows and/or columns of microstructures on the substrate 114a. The interstitial filler 114d may fill a region between separate microelectrodes 114c. The interstitial filler 114d may include a polymer. In one embodiment the interstitial filler 114d may include a photoresist material. In one embodiment the interstitial filler 114d may include polyimide. In one embodiment, the interstitial filler 114d may include bisphenol A novolac epoxy. The interstitial filler 114d may be deposited on the substrate 114a and/or around the intermediate layers 114b and microelectrodes 114c by sputtering and or spin-coating.

In various embodiments, the first sensor 112 and/or the second sensor 114 may measure the same physiological manifestation, characteristic, constituent, and so forth, by different physical mechanisms. For example, the first sensor 112 may be an optical sensor and the second sensor 114 may be an impedance sensor. A signal generated by the first sensor 112 over a time domain may indicate a change in hydration of the subject over the time domain by detecting changes to the scattering of light by the subject's skin. A second signal generated by the second sensor 114 over the time domain may also indicate the change in the subject's hydration over the time domain. However, the second sensor 114 may detect changes to the impedance of the subject's skin. Accordingly, the first signal (i.e. the signal generated by the first sensor) may be a first time-variant current reflecting changes in optical scattering, and the second signal may be a second time-variant current reflecting changes in impedance. Similar changes in the first time-variant current and the second time-variant current over the same time domain may reflect changes to the same physiological characteristic of the subject.

Figures 2A, 2B:
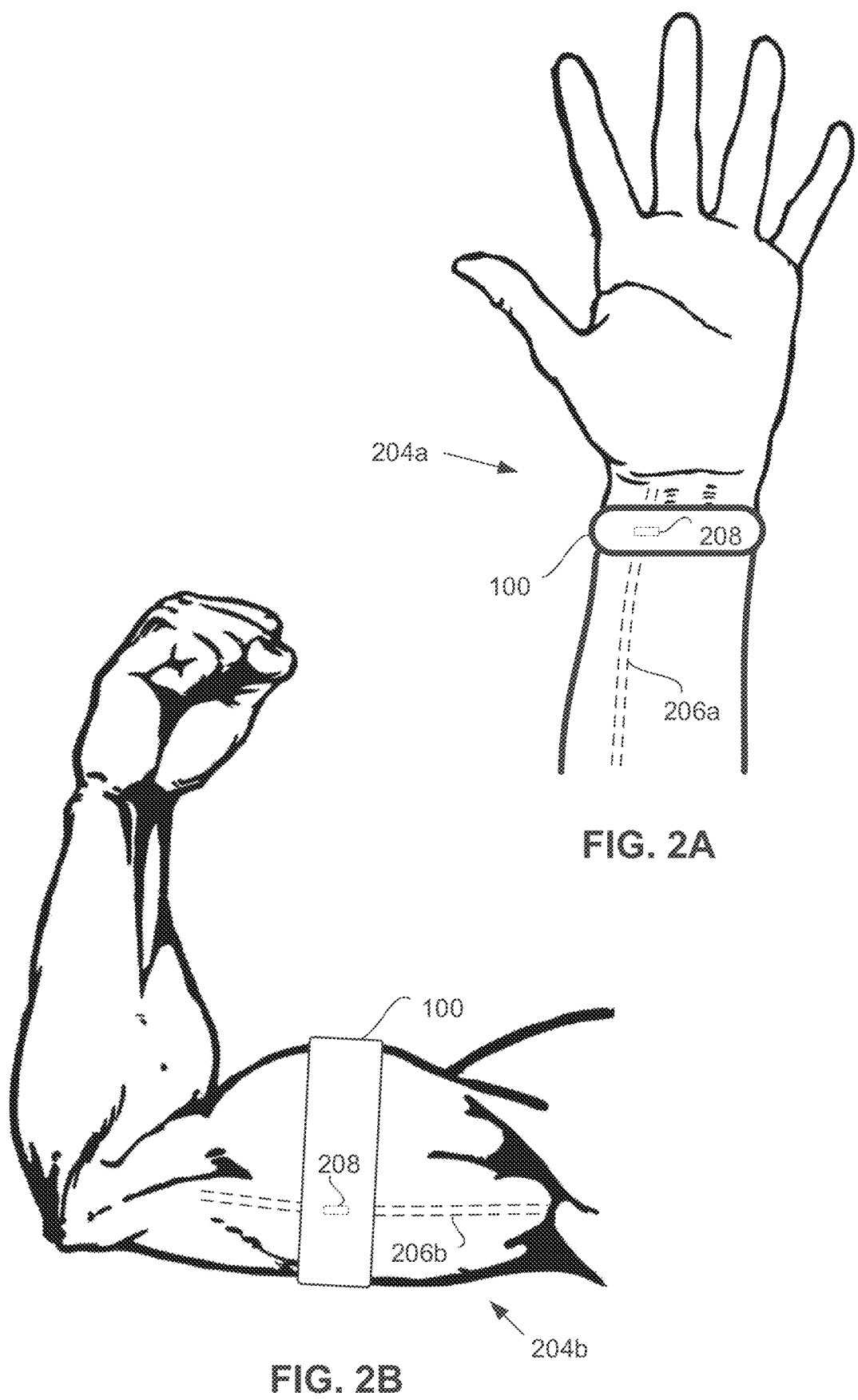
FIG. 2A illustrates a wearable device on a wrist of a subject, according to an embodiment.
FIG. 2B illustrates a wearable device on an arm of the subject, according to an embodiment.

FIG. 2A illustrates the wearable device 100 on a wrist 204a of a subject, according to an embodiment. Some of the features in FIG. 2A may be the same as or similar to some of the features in the other FIGs. described herein as noted by same and/or similar reference characters, unless expressly described otherwise. Additionally, reference may be made to features shown in any of the other FIGs. described herein and not shown in FIG. 2A. The wrist 204a may include a first muscular-walled tube 206a. The first muscular-walled tube 206a may be, in an embodiment, a vein or an artery. The wearable device 100 may have an integrated biometric sensor 208. The biometric sensor 208 may include the first sensor 112 and/or the second sensor 114. For example, the biometric sensor 208 may include an impedance sensor and/or a miniaturized spectrometer.

The wearable device 100 may be positioned on the wrist 204a so that the biometric sensor 208 may be positioned over the muscular-walled tube 206a. In an embodiment, the first muscular-walled tube 206a may be positioned in the wrist 204a approximate to an underside of the wrist 204a. For example, the first muscular-walled tube 206a may be positioned in the wrist 204a between a dermal layer of the wrist 204a and one or more bones in the wrist 204a. The biometric sensor 208 may be positioned against the underside of the wrist 204a. This may optimize an accuracy and/or precision of a measurement taken by the biometric sensor 208 from the muscular-walled tube 206a. The wearable device 100 may use the measurements to determine a physiological condition of the subject. Positioning the biometric sensor 208 against the underside of the wrist may also reduce a chance of the biometric sensor 208 being struck or otherwise damaged in a way that may affect the accuracy and/or precision of the measurement taken by the biometric sensor 208. For example, an outside of the wrist 204a may be exposed to other surfaces against which the wearable may be struck, whereas an underside of the wrist 204a may be less likely to strike other surfaces because it faces towards a body of the subject.

FIG. 2B illustrates the wearable device 100 on an arm 204b of the subject, according to an embodiment. Some of the features in FIG. 2B may be the same as or similar to some of the features in the other FIGs. described herein as noted by same and/or similar reference characters, unless expressly described otherwise. Additionally, reference may be made to features shown in any of the other FIGs. described herein and not shown in FIG. 2B. The arm 204b may include a second muscular-walled tube 206b. The second muscular-walled tube 206b may be, in an embodiment, a vein or an artery. The wearable device 100 may be positioned on the arm 204b so that the biometric sensor 208 may be positioned over the second muscular-walled tube 206b.

In various embodiments, the wearable device 100 may be worn by the subject on another body part such as a hand of the subject, a forearm of the subject, an elbow of the subject, a chest of the subject, a neck of the subject, a head of the subject, a torso of the subject, a waist of the subject, a thigh of the subject, a calf of the subject, a knee of the subject, an ankle of the subject, or a foot of the subject. Accordingly, the body part may include a muscular-walled tube. The muscular-walled tube may include an ulnar artery, a radial artery, a brachial artery, a basilic vein, a cephalic vein, an axillary artery, an axillary vein, a carotid artery, a jugular vein, an iliac artery, a femoral artery, a femoral vein, a tibial artery, a great saphenous vein, a *dorsalis* pedis artery, an arch of foot artery, or a temporal artery.

In various embodiments, the biometric sensor 208 may be pressed against the skin surface of the body part. The biometric sensor 208 and/or wearable device 100 may be positioned on the body part over a region of the body part where the muscular-walled tube may be closest to the skin surface for the body part. The biometric sensor 208 may be positioned against the body part where the muscular-walled tube may be positioned between the biometric sensor 208 and a skeletal structure of the body part. This may minimize the distance between the biometric sensor 208 and the muscular-walled tube, which in turn may optimize one or more biometric measurements taken by the biometric sensor 208 from the muscular-walled tube. In various embodiments, the biometric sensor 208 and/or the wearable device 100 may be positioned on the body part over a region of the body part where the skeletal structure is positioned between the skin surface and the muscular-walled tube. This may maximize the distance between the biometric sensor 208 and the muscular-walled tube, which in turn may minimize effects of the muscular-walled tube on measurements taken by the biometric sensor 208. For example, the subject may desire to measure a relatively static physiological condition, physiological parameter, and/or physiological constituent such as a bone density of the subject and/or a body fat percentage of the subject. The muscular-walled tube may be dynamic and may interfere with measuring the static physiological condition, physiological parameter, and/or physiological constituent. Accordingly, maximizing the distance between the biometric sensor 208 and the muscular-walled tube may result in more accurate and/or precise measurements of the static physiological condition, physiological parameter, and/or physiological constituent. In various embodiments, the biometric sensor 208 and/or the wearable device 100 may be positioned on the body part such that the biometric sensor 208 may be approximate to the muscular-walled tube and the skeletal structure such that the muscular-walled tube is not between the skeletal structure and the biometric sensor 208 and the skeletal structure is not between the muscular-walled tube and the biometric sensor 208.

FIGS. 3A-B illustrate an example of a sensor interrogating a physiological characteristic of a subject, according to an embodiment. Some of the features in FIGS. 3A and/or B may be the same as or similar to some of the features in the other FIGs. described herein as noted by same and/or similar reference characters, unless expressly described otherwise. Additionally, reference may be made to features shown in any of the other FIGs. described herein and not shown in FIGS. 3A and/or B. The sensor may be an impedance sensor, e.g. the second sensor 114 illustrated in FIGS. 1A-C. FIG. 3A illustrates impedance paths 302 aligned parallel to an artery 304. FIG. 3B illustrates the impedance paths 302 aligned perpendicular to the artery 304. A first set of electrodes 306 may be electrically coupled to a current source 308. In an embodiment, the current source 308 may include a voltage to current converter. A second set of electrodes 310 may be electrically coupled to a voltmeter 312. In an embodiment, the voltmeter 312 may include an operational amplifier. The first set of miniaturized electrodes 306 may cause a current to be passed through skin 314 of the subject, a subcutaneous tissue 316, and/or the artery 304. The second set of miniaturized electrodes 310 may be placed between the two electrodes of the first set of miniaturized electrodes 306 to measure a voltage between the two electrodes of the first set of miniaturized electrodes 306. The resulting voltage may be subsequently used to determine an impedance of the skin 314, the subcutaneous tissue 316, and/or the artery 304. In an embodiment, an impedance of the artery 304 may include an impedance of substances found within the artery 304, such as blood and/or various blood constituents.

Arrows 318 may indicate an expansion of the artery 304 as blood is pumped through the artery 304 by the heart of the subject. The artery may expand according to the heartbeat of the heart. Expansion of the artery 304 may change a volumetric composition of a volume for which the impedance is measured. The change in the volumetric composition may change the impedance in cadence with the heartbeat. Accordingly, changes in impedance may be caused by the heartbeat and may be correlated directly with a condition, parameter, and/or constituent of the heart and/or circulatory system.

Figure 3C:
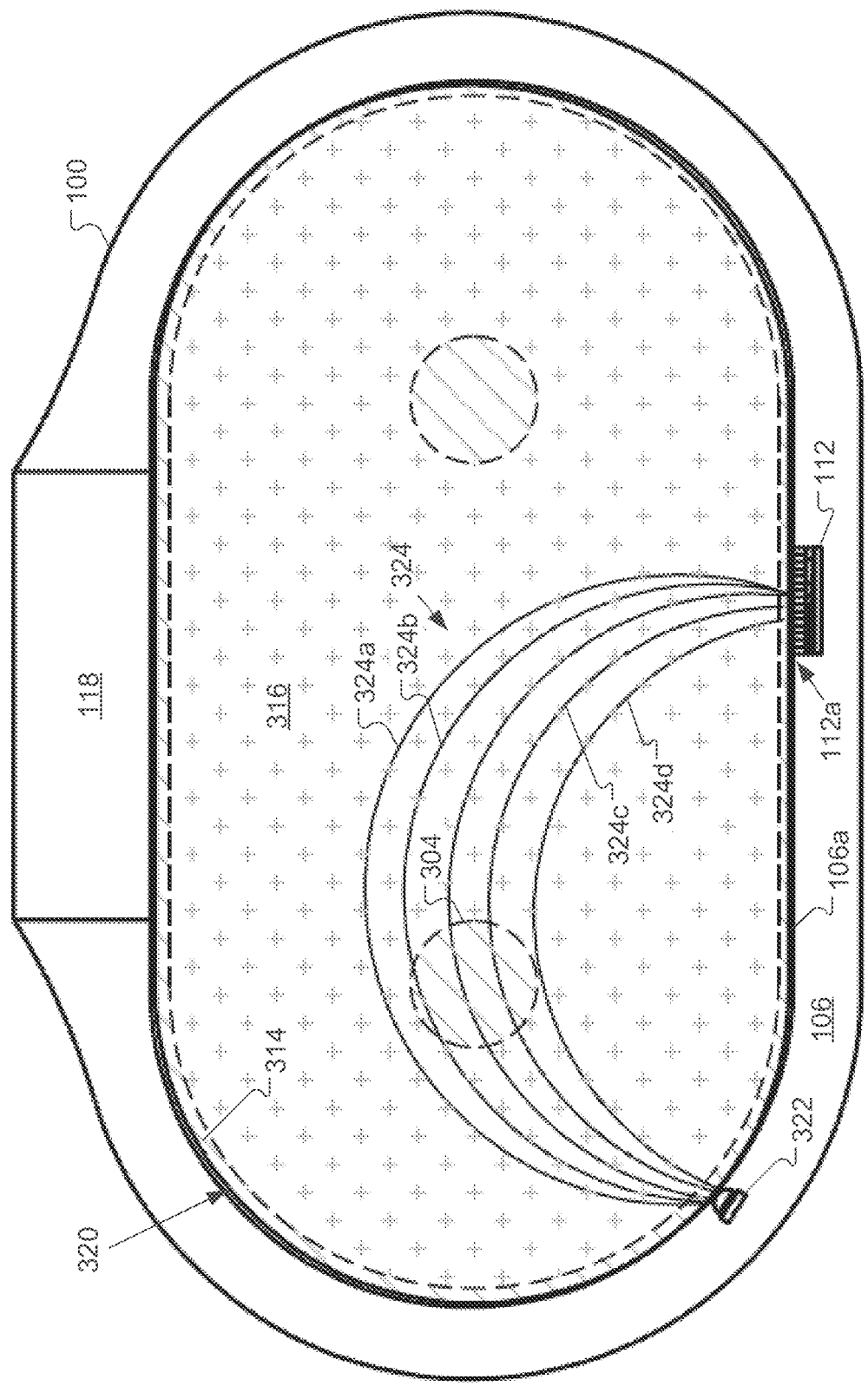
FIG. 3C illustrates another example of a different sensor interrogating the same physiological characteristic of the subject as illustrated in FIGS. 3A-B, according to an embodiment.

FIG. 3C illustrates another example of a different sensor interrogating the same physiological characteristic of the subject as illustrated in FIGS. 3A-B, according to an embodiment. Some of the features in FIG. 3C may be the same as or similar to some of the features in the other FIGs. described herein as noted by same and/or similar reference characters, unless expressly described otherwise. Additionally, reference may be made to features shown in any of the other FIGs. described herein and not shown in FIG. 3C. In an embodiment, the wearable device 100 may be disposed around a body part 320 of the subject with a light source 322 emitting light 324 through the body part 320 to the first sensor 112. The body part 320 may include the skin 314, the subcutaneous tissue 316, and the artery 304. In an embodiment, the body part 320 may include a wrist of the subject. The wearable device 100 may include the band 106 which may wrap around the body part 320. The light source 322 may be positioned within the band 106 to face the body part 320 when the band 106 is wrapped around the body part 320. The first sensor 112 may include a miniaturized spectrometer. The first sensor 112 may be disposed within the band 106 to face the body part 320 as the band 106 is wrapped around the body part 320.

In an embodiment, the light source 322 may be at least partially exposed from the band 106. For example, an illuminating portion of the light source 322 may be exposed from the band 106 such that the illuminating portion of the light source 322 protrudes from the band 106 or is set within the band 106, forming a discontinuity in an inside surface 106a of the band 106. In another example, the illuminating portion of the light source 322 may be flush with the inside surface 106a of the band 106 to form a continuous surface with the inside surface 106a. In an embodiment, the first sensor 112 may be at least partially exposed from the band 106. For example, a surface of the first sensor 112 may be flush with the inside surface 106a of the band 106 such that the surface of the first sensor 112 and the inside surface 106a of the band 106 form a continuous surface. In another example, the first sensor 112 may protrude from the band 106. The band may encompass a portion of the first sensor 112, and a portion of the first sensor 112 may extend from the band 106. In yet another example, the first sensor 112 may be set within the band 106, forming a cavity in the band 106 over the first sensor 112. The cavity in the band 106 may form a discontinuity in the inside surface 106a of the band 106.

In an embodiment, the light source 322 may emit the light 324 omnidirectionally or partially omnidirectionally. For example, the light source 322 may emit the light 324 omnidirectionally beyond the inside surface 106a of the band 106. In another embodiment, the light 324 may be channeled and/or directed in a direction and/or within a range of directions corresponding to polar and/or azimuthal ranges. For example, the light 324 may be emitted in a 360-degree polar range and a 180-degree azimuthal range. The polar range may vary from 1 degree to 360 degrees. The azimuthal range may vary from 1 degree to 300 degrees. In an embodiment, the light 324 may be a ray of unidirectional light. The light 324 as initially emitted from the light source 322 may include a spectrum of wavelengths. The light 324 may be monochromatic or polychromatic. The light 324 may be emitted from the light source 322 at a specific, selected, and/or known intensity level, where the intensity level may be known to a processing device disposed in the housing 118 and electrically coupled to the light source 322 and/or the first sensor 112. For example, the intensity level of the light 324 may be stored in transitory and/or non-transitory memory and/or into the processing device (such as in a cache of the processing device), or the intensity level of the light 324 may be measured and communicated to the processing device when the light 324 is emitted from the light source 322.

The light 324 may be reflected as it passes through the body part 320 so that it strikes the first sensor 112. As described earlier, the light source 322 may emit the light 324 omnidirectionally. The light 324 may include light rays 324a-d. The light rays 324a-d may follow different paths through the body part 320, and in an embodiment, the light rays 324a-d may each be reflected towards the first sensor 112. As the light rays 324a-d are emitted from the light source 322, each light ray 324a-d may have the same and/or similar light profile as each other light ray 324a-d. The light profile may include the wavelength of the light 324, the intensity of the light 324, and/or the phase of the light 324. As the light rays 324a-d pass through the body part 320, the light profile for each light ray 324a-d may change differently from each other light ray 324a-d. Accordingly, each light ray 324a-d may have a different light profile from each other light ray 324a-d as it impinges on (i.e. strikes) the first sensor.

As the light 324 travels through the body part 320, the light 324 may reflect off a variety of tissues and/or other constituents within the body part 320. The light 324 may follow a non-linear path through the body part 320 from the light source 322 to the first sensor 112. In an embodiment, the path the light 324 follows may go through the skin 314, the subcutaneous tissue 316, and/or the artery 304. As the light 324 passes through the body part 320, constituents and/or tissues of the body part 320 may absorb and/or reflect various wavelengths of the light 324. For example, the artery 304 may include a vein or an artery. The vein or the artery may carry blood within the vein or artery. The blood may include various constituents, including red blood cells, white blood cells, water, platelets, glucose, mineral ions, hormones, proteins, and so forth. The various constituents of the blood may strongly absorb, transmit, and/or reflect light in different ways. For example, red blood cells may strongly absorb wavelengths ranging from 320 nanometers (nm) to 450 nm. Blood glucose may strongly reflect and/or transmit wavelengths ranging from 725 nm to 775 nm, from 1050 nm to 1100 nm, and/or from 1550 nm to 1700 nm.

Each wavelength may reflect a blend of constituents. Each constituent of blood may have a unique absorbance corresponding to a single wavelength. A resulting intensity of a wavelength passing through the vein or the artery may be the result of the combined effects of each of the constituent's absorbance coefficients and the respective concentrations of the constituents. The Beer-Lambert Law may be one way of concretely quantifying this effect. Quantifying the relative amount of the various blood constituents may be accomplished by determining relative intensities of several wavelengths and determining which combination of each of the constituents would give the net result. The quantification may be accomplished by a multivariate regression analysis and/or other machine learning algorithm based on an iterative optimization problem to reduce error from a training set.

The first sensor 112 may collimate the light rays 324a-d such that the light 324 striking the first sensor surface at a roughly normal angle may pass into the first sensor 112. For example, light striking the first sensor surface at an angle ranging from 60 degrees to 90 degrees, from 70 degrees to 90 degrees, from 75 degrees to 90 degrees, from 80 degrees to 90 degrees, and/or from 85 degrees to 90 degrees may pass into the first sensor 112. The first sensor 112 may filter the light rays 324a-d and may detect one or more features of the light profile of each light ray 324a-d. The detected features may be communicated to the processing device. The processing device may perform one or more of various calculations and/or functions using and/or based on a comparison and/or analysis of the light profile of the light 324 as emitted from the light source 322 and light profiles of the light rays 324a-d detected by the first sensor 112.

In various embodiments, the outputs of the first sensor 112 and/or the second sensor 114 may include a current signal and/or a voltage signal. For example, the voltmeter 312 may output a voltage corresponding in amplitude to the impedance of the skin 314, the subcutaneous tissue, and/or the artery 304. The impedance voltage may be variable across a given time domain. As another example, the optical sensor of the first sensor 112 may output a voltage corresponding in amplitude to the intensity of the light rays 324a-d. The light intensity voltage may also be variable across the time domain.

Figure 4A:
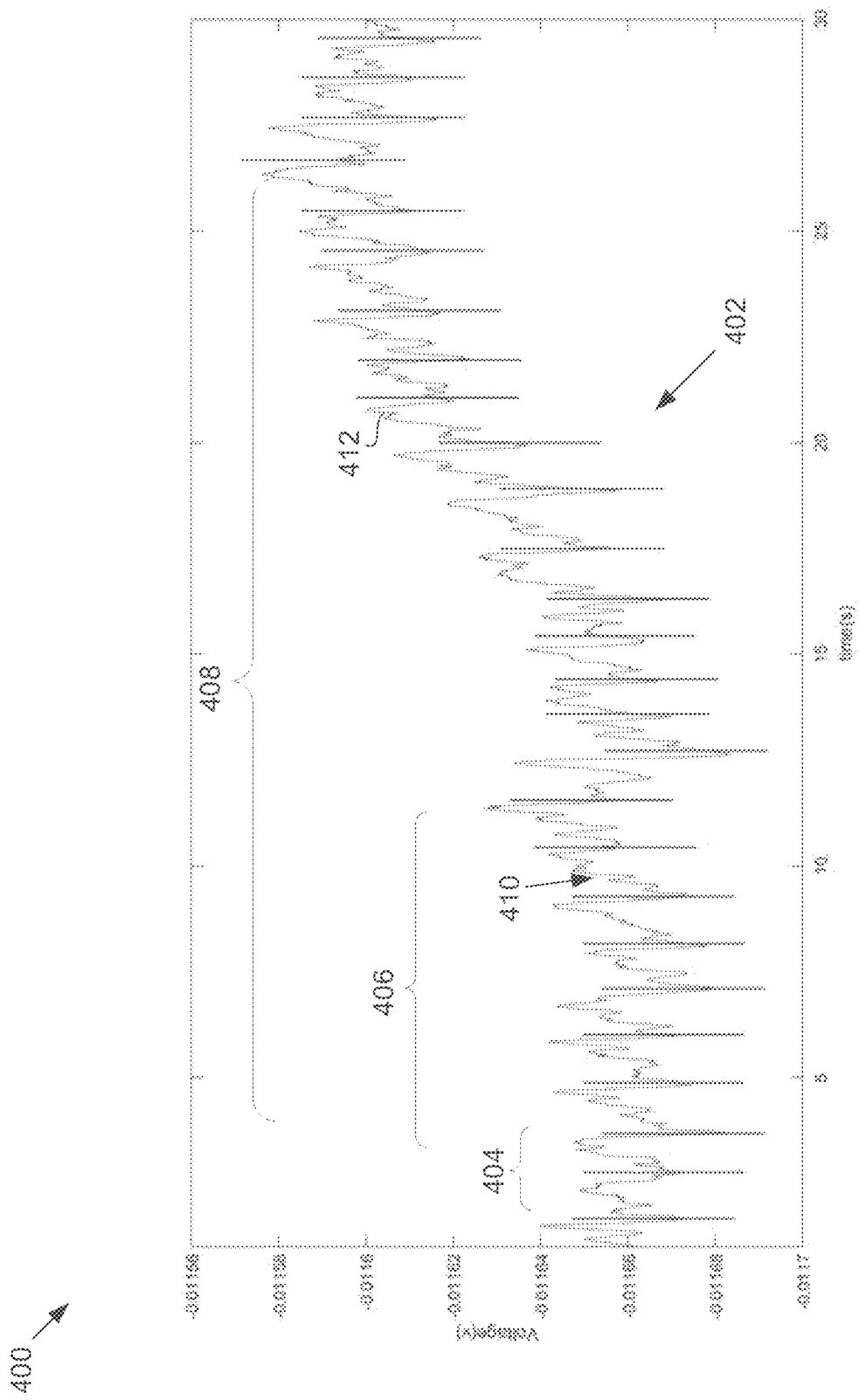
FIG. 4A illustrates a graph of a heartbeat waveform indicated by a voltage signal as a function of time, according to an embodiment.

FIG. 4A illustrates a graph 400 of a heartbeat waveform 402 indicated by a voltage signal as a function of time, according to an embodiment. Some of the features in FIG. 4A may be the same as or similar to some of the features in the other FIGs. described herein as noted by same and/or similar reference characters, unless expressly described otherwise. Additionally, reference may be made to features shown in any of the other FIGs. described herein and not shown in FIG. 4A. In one example, a structure of a body part of a user, such as an artery, may include a dynamic internal feature that causes variability in an impedance of the structure. The dynamic internal feature may include a variable volume or material constituency, such as an amount of blood in the artery or the diameter or size of the artery.

The heartbeat waveform 402 may be used by a processing device to isolate and/or identify a physiological condition, a physiological parameter, and/or a physiological constituent of a user of a wearable device such as the wearable device 100. The heartbeat waveform 402 may fluctuate over a variety of timeframes. The timeframes may include a first timeframe 404, a second timeframe 406, and a third timeframe 408. The heartbeat waveform 402 may correspond to a change in the volume of blood within a body part adjacent to the impedance sensor. The body part may include a muscular-walled tube for carrying blood, such as a vein or artery. The heartbeat waveform 402 may be represented as a change in voltage. As the volume of blood within the body part increases, the voltage measured by the impedance sensor may increase. As the volume of blood within the body part decreases, the voltage measured by the impedance sensor may decrease. A shape of the heartbeat waveform 402 may include noise 410. The noise 410 may correspond to one or more other physiological and/or non-physiological factors such as feedback and/or electronic noise within the impedance sensor, electrical signals within the body not generated by the impedance sensor, physiological elements and/or factors, and so forth.

Voltage changes within the various timeframes may correspond in time to changes in physiological features that may affect a volume of blood in the user's vein and/or artery. For example, a short timeframe such as the first timeframe 404 may correspond to the user's heartbeat and/or breathing. Viewing a shorter timeframe may illuminate one or more heart conditions, such as the effectiveness of a mitral valve of the heart as indicated by a dicrotic notch 412. A longer timeframe such as the second timeframe 406 may correspond to a sympathetic response of the user or a posture change of the user. One such sympathetic response may include vasoconstriction due to the user being exposed to cold. One such posture change may include the user lowering the body part relative to the user's heart and/or raising the body part relative to the user's heart. The longer timeframe may correspond to the user performing a Valsalva maneuver, such as when lifting weights. A yet longer timeframe such as the third timeframe 408 and timeframes longer than the third timeframe 408 may indicate a peripheral disease which may affect volumetric flow of blood and/or an amount of current impeded by the blood. For example, increased levels of blood glucose may decrease the impedance of the blood. Sustained levels of decreased impedance may indicate glucose is not being removed from the blood sufficiently. Excess blood glucose may lead to one or more health conditions such as blood vessel damage, organ damage, and so forth.

During the first timeframe 404, the voltage of the measurement may vary by as much as $3 \times 10^{-5}$ Volts (V) over approximately 3 seconds. A local maximum within the first timeframe 404 may correspond to the user's heart contracting, forcing blood out of the heart and through the artery and/or vein. A local minimum within the first timeframe 404 may correspond to the user's heart expanding and drawing blood from the artery and/or vein. During the second timeframe 406, the voltage of the measurement may vary by as much as $6 \times 10^{-5}$ V over approximately 10 seconds. The second timeframe 406 may correspond to a physiological condition, physiological parameter, and/or physiological constituent closely related to the user's heartbeat. A relative increase of the local maximums and/or the local minimums may correspond to, for example, vasodilation. During the third timeframe 408, the voltage of the measurement may vary by as much as $1 \times 10^{-4}$ V over approximately 25 seconds. The third timeframe 408 may correspond to a physiological condition, physiological parameter, and/or physiological constituent unrelated to the user's heartbeat, such as the hydration condition of the user. Longer timeframes may correspond to more a static physiological condition, physiological parameter, and/or physiological constituent of the user, such as body fat percentage and/or bone density.

The heartbeat waveform 402 may be passed to a processing device that may perform a function on the heartbeat waveform 402 to separate constituent waveforms of the heartbeat waveform 402. The function may include, for example, a regression analysis. As another example, the function may include a correlation analysis with a second simultaneously-measured heartbeat waveform that is measured by a different physical mechanism than impedance. The processing device may identify a timeframe associated with an individual constituent waveform to identify a type of physiological condition, physiological parameter, and/or physiological constituent to which the constituent waveform corresponds. In an embodiment, the processing device may select constituent waveforms on a timeframe corresponding to the user's heartbeat to determine the constituent of the user's blood. In an embodiment, the processing device may select constituent waveforms on a timeframe much larger than a timeframe of the user's heartbeat to determine a physiological condition of the user's skin. In an embodiment, the processing device may select a constituent waveform based on the shape of succeeding crests and valleys. The shape of succeeding crests and valleys may correspond to one or more of a diastole, a systole, and a dichroic notch of the user's heartbeat.

FIG. 4B is a pictorial representation of a correlation of two different types of measurements, according to an embodiment. Some of the features in FIG. 4B may be the same as or similar to some of the features in the other FIGs. described herein as noted by same and/or similar reference characters, unless expressly described otherwise. Additionally, reference may be made to features shown in any of the other FIGs. described herein and not shown in FIG. 4B.

In various implementations, sensor data from two or more sensors may be obtained. The sensors may be positioned relatively close to each other, such as in a wristband on an underside of the wrist, a headband near the temple, a chest band over the heart, and so forth. The sensors may be different types of sensors. For example, a first sensor may be an impedance sensor and a second sensor may be an optical sensor with a light emitter. The first sensor may be susceptible to signal noise such as electronic interference, a variation of certain physiological parameters other than a parameter of interest, movement of the sensor, and so forth. The second sensor may be susceptible to different signal noise. The second sensor may be susceptible to similar signal noise from different sources (e.g., the electronic interference may have different sources, and so forth).

Measurement data 414 from the first sensor may be indicative of a first physiological parameter, a second physiological parameter, and first noise (e.g., signal variation not attributable to a feature of interest). Measurement data 416 from the second sensor may be indicative of the first physiological parameter, a third physiological parameter, and second noise. The first noise may be attributable to at least some sources that are different from the sources of the second noise. Because the first noise and the second noise are independent, combining the noise may result in the combined noise being diminished relative to the combined signal for the first physiological parameter. Accordingly, the measurement data 414 and the measurement data 416 may be correlated 418 to produce combined measurement data 420 where data indicative of the first physiological parameter is amplified or relatively unperturbed and data indicative of the first noise and the second noise is dampened.

In various implementations, the noise may be irrelevant to the physiology of the subject. The noise may include feedback from one or more electronic elements of the sensor, the processor, or, in general, the electronic system into which the sensor is incorporated. The noise may include interference caused by environmental factors such as a temperature or pressure change of the subject's ambient environment. The noise may be induced by physical movement and/or shifting of the measurement device (e.g., the wearable device 100) relative to the subject. For example, a shift of an impedance sensor away from an artery may change the impedance, such as by increasing the impedance, in a way different from, and/or on a different time scale than, the volumetric change of the artery as the subject's heartbeats. The change in the impedance and/or the shape of the related signal over time may persist until the sensor is realigned with the artery. The noise may include a superposition of noise from various sources.

A signal over a given time domain may include modulation due to a variety of physiological characteristics. The signal may include modulation due to the subject's heart beating, thus changing a volume of blood in a given body part over a range of less than a second to a few seconds. The signal may include modulation due to variation in one or more constituents in the subject's blood. The constituents may include glucose, hematocrit, a hormone such as adrenaline, oxygen, alcohol, water, and so forth. The signal may, for example, include modulation due to the subject's blood oxygenation level changing.

Physiological characteristics may be differentiable from each other by the physical mechanism used to generate the signal. For example, a pressure sensor may indicate a change in a volume of a region of an artery. An optical sensor may indicate the volume change and may also include modulation due to a changing blood oxygen level of the subject. The subject's blood oxygen level may modulate over the same time domain as the volume of the artery modulates due to the subject's heartbeat. The optical sensor may output a signal that includes a superposition of the arterial volumetric modulation and the blood oxygen level modulation. The pressure sensor may output a signal that includes the arterial volumetric modulation.

When the two signals are compared, the portion of the optical signal modulation due to the subject's blood oxygen level changing may be isolated in the optical signal. In such a manner, a signal-to-noise ratio (SNR) for a particular biological constituent or physiological characteristic of interest may be increased, thereby allowing modulation of the biological constituent or physiological characteristic to be identified independently of other comodulating constituents or characteristics.

A pulse of the subject may form a baseline for identifying and measuring a change in blood constituents. Many blood constituents, such as glucose, hormones, blood oxygenation level, blood alcohol content, and so forth, may modulate over longer time domains than a single pulse width of a subject's heartbeat. In cases where the constituent modulates over a similar time domain, the constituent may modulate out of phase (e.g. out of rhythm) with the subject's heartbeat. To accurately isolate the modulation of other blood constituents from the subject's pulse, it may be useful to have a reference signal for the subject's pulse.

An interrogation signal may be acquired using a first physical mechanism (i.e., a first type of sensor that operates based on a first physical property). The interrogation signal may include superpositions on the pulse signal of one or more other modulations due to one or more blood constituents. The interrogation signal may include superpositions on the pulse signal of noise that is unrelated to a constituent of interest. The interrogation signal may be recorded by a processor as, for example, voltage amplitudes at discrete times. The voltage and time information may be indicated in measurement data. The measurement data may be stored in a memory device and/or transmitted to a remote server such as a cloud-based server.

A reference signal may be acquired using a second physical mechanism (i.e., a second type of sensor that operates based on a second physical property that is different from the first physical property). The reference signal may include superpositions on the pulse signal of noise that is unrelated to the constituent of interest and/or unrelated to the noise in the interrogation signal. The reference signal may be recorded by a processor as, for example, voltage amplitudes at discrete times. The voltage and time information may be indicated in measurement data. The measurement data corresponding to the reference signal may be separate from the measurement data corresponding to the interrogation signal. The reference signal measurement data may be stored in a memory device and/or transmitted to a remote server such as a cloud-based server.

The interrogation signal may be expressed as a linear combination of signal (S) and noise (n), each as a function of time, as expressed in equation (1):

$$\text{Interrogation Signal} = S(t) + n(t). \tag{1}$$

Similarly, the reference signal may be expressed as a linear combination of signal (S') and noise (n'), each as a function of time, as expressed in equation (2):

$$\text{Reference Signal} = S'(t) + n'(t). \tag{2}$$

The amount and/or strength of the noise on the reference signal may be significantly smaller than the amount and/or strength of the noise on the interrogation signal, as expressed in equation (3):

$$n(t) \gg n'(t). \tag{3}$$

The amount and/or strength of the signal portion in the interrogation signal may be approximately proportional to the amount and/or strength of the signal portion of the reference signal, as expressed in equation (4):

$$S(t) \sim S'(t). \tag{4}$$

The amount and/or strength of the signal portions of the interrogation signal and the reference signal may be significantly larger than the amount and/or strength of the noise portions of the interrogation signal and the reference signal, as expressed in equation (5):

$$S(t), S'(t) \gg n(t), n'(t). \tag{5}$$

The noise on the interrogation signal may be of a different type and/or may be independent of the noise on the reference signal.

The noise (n(t), n'(t)) may be reduced and/or eliminated by correlating the interrogation signal with the reference signal. A correlation (C) of the interrogation signal and the reference signal may be expressed as shown in equation (6) below:

$$C = \frac{1}{T}\int_{t_0}^{t_n}(S(t) + n_S(t))(R(t) + n_R(t))dt, \tag{6}$$

where T is the time domain from $t_0$ to $t_n$. The interrogation signal may be time-shifted from the reference signal, and/or an alignment of the interrogation signal with the reference signal may be unknown. In such cases, the noise may be reduced and/or eliminated by a cross-correlation function as shown in equation (7) below:

$$C = \int_{-\infty}^{\infty}\overline{(S(t) + n_S(t))}(R(t+\tau) + n_R(t+\tau))d\tau, \tag{7}$$

where $\tau$ is the time delay between the interrogation signal and the reference signal. The cross-correlation function may be iterated for multiple values of $\tau$ until the interrogation signal and the reference signal are aligned. As used herein, the correlation function and the cross-correlation function may be referred to as correlation functions. The correlation may be a function that amplifies and/or maintains the similarities between the interrogation signal and the reference signal and diminishes the differences. Accordingly, the noise that does not correlate between the interrogation signal and the reference signal may be minimized and/or eliminated.

The signal portion of the interrogation signal may be modulated by a constant function ($c_n$), as expressed in equations (8) and (9):

$$\text{Interrogation Signal}_n = c_n S(t), \tag{8}$$

$$\text{Interrogation Signal}_{n+1} = c_{n+1} S(t), \tag{9}$$

where the subscripts denote a time period and a subsequent time period. The constant function during the first time period (e.g. $c_n$) may be different than the constant function during the subsequent time period (e.g. $c_{n+1}$). The difference may be due to a change in one or more of the constituents of interest such as blood glucose, blood oxygen, hematocrit, blood alcohol, hormones, and so forth. A difference between the constant function during the first time period and the constant function during the second time period may indicate a change in the one or more constituents of interest.

The constant function may be time-dependent for one or more of the constituents of interest. Accordingly, amounts of the time-dependent constituents of interest may vary during the time periods (e.g. n, n+1, and so forth). To calculate the difference between the constant function during the first time period and the second time period, a first average for the constant function may be calculated for the first time period and a second average for the constant function may be calculated for the second time period. The difference may be calculated between the first average and the second average.

Contributions by the one or more constituents of interest to the change in the constant function may be determined by performing a multivariate and/or spectral analysis. For example, the interrogation signal may be generated by an optical sensor. A light may emit light ranging from 1700 nm to 400 nm. The optical sensor may include sensor regions corresponding to constituents of interest that scatter light in the range of 1700 nm to 400 nm. One sensor region may correspond to glucose and may be sensitive to approximately 1600 nm-wavelength light. A signal strength generated by the 1600 nm sensor region may correspond to a glucose level in the subject's blood. A signal strength generated by another sensor region may correspond to another constituent of interest in the subject's blood.

The interrogation signal may be modulated by a first constant function and/or the reference signal may be modulated by a second constant function. The first constant function may be a function of a first set of physiological characteristics. The second constant function may be a function of a second set of physiological characteristics. The first set of physiological characteristics may include characteristics $A_1$ through $A_n$. The second set of physiological characteristics may include characteristics $A_1$ through $A_{n-1}$. The physiological characteristic $A_n$ may be identified by correlating the interrogation signal and the reference signal.

The interrogation signal may include modulation due to a variety of physiological characteristics. The reference signal may include modulation due to a targeted physiological characteristic. For example, a physiological characteristic of interest may be the blood glucose level of the subject. The interrogation signal may be generated by an impedance sensor. The impedance sensor may output an impedance of a region of the subject's body. The impedance may modulate due to a variety of physiological characteristics, including variation in the subject's blood glucose levels. The interrogation signal may include noise that is specific to the impedance sensor and noise due to other physiological characteristics not of interest.

The reference signal may be generated by an optical sensor sensitive to wavelengths of light that are tuned for glucose (e.g., 1600 nm). The reference signal may include other noise that is independent of the noise on the interrogation signal. The reference signal may not include noise that is related to noise in the interrogation signal, including modulation due to the other physiological characteristics not of interest. correlation of the interrogation signal with the reference signal may yield a signal that enhances what the two signals have in common, e.g., the glucose modulation, and diminishes what the two signals do not have in common, e.g., the noise.

Figure 5:
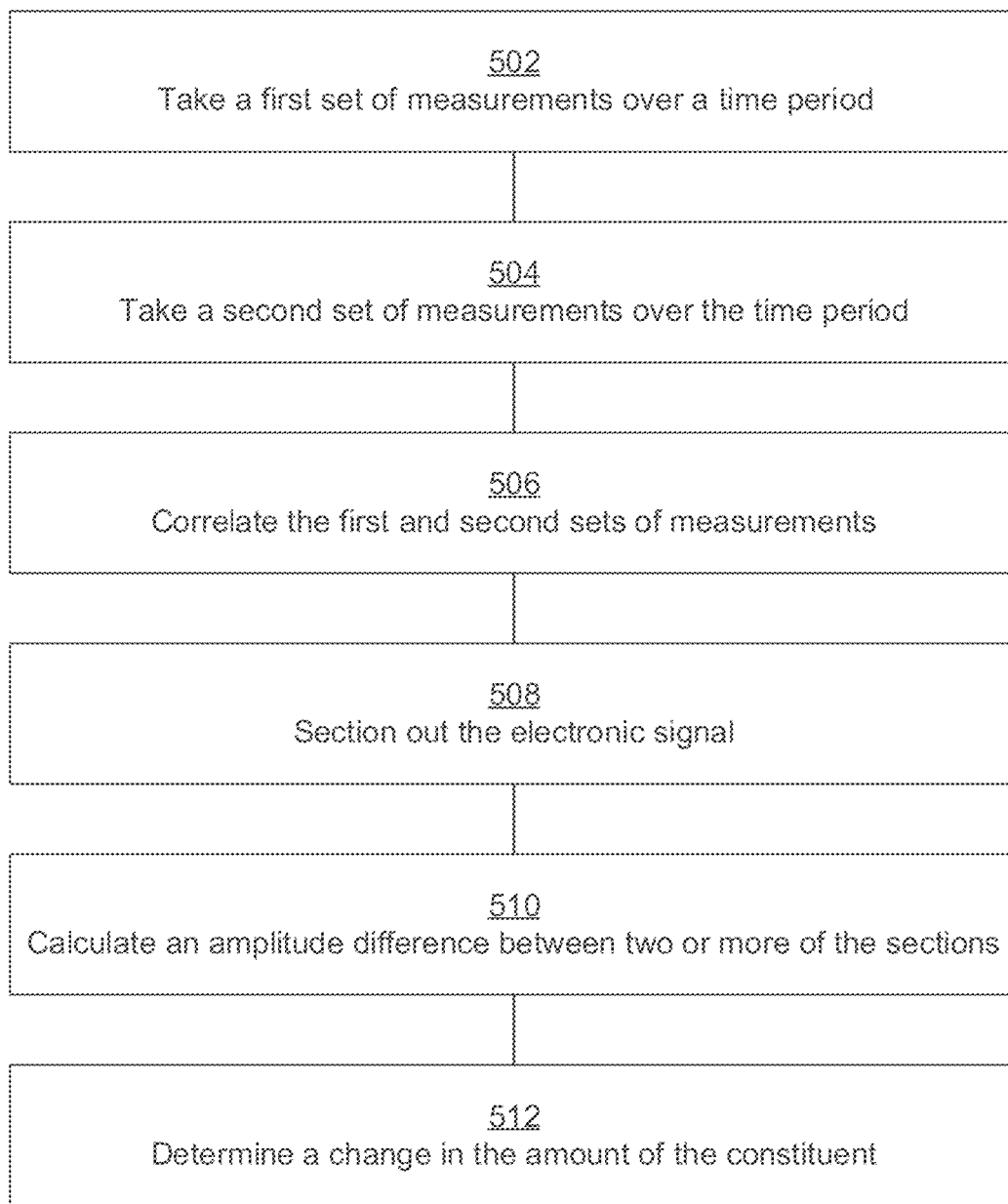
FIG. 5 illustrates a method of determining a change in a constituent of interest using two correlated measurement signals, according to an embodiment.

FIG. 5 illustrates a method 500 of determining a change in a constituent of interest using two correlated measurement signals, according to an embodiment. Some of the features in FIG. 5 may be the same as or similar to some of the features in the other FIGs. described herein as noted by same and/or similar reference characters, unless expressly described otherwise. Additionally, reference may be made to features shown in any of the other FIGs. described herein and not shown in FIG. 5.

The method 500 may include taking a first set of measurements over a time period by a first sensor (block 502). The first sensor may be integrated into a wearable device such as the wearable device 100. The first sensor may measure a physiological characteristic of a subject wearing the wearable device by a first physical mechanism. The first set of measurements may be indicated by a first electronic signal. The first electronic signal may be characterized by a varying amplitude. The method 500 may include taking a second set of measurements over the time period by a second sensor (block 504). The second sensor may be integrated into the wearable device adjacent to the first sensor. The second sensor may measure the physiological characteristic of the subject by a second physical mechanism that is different than the first physical mechanism.

The method 500 may include removing noise from the first set of measurements and/or the second set of measurements by correlating the first set of measurements with the second set of measurements (block 506). The method 500 may include sectioning out the electronic signal (block 508). The electronic signal may be sectioned out into two sections, or three sections, or into four sections, and so forth. The first section may have a first average amplitude. The second section may have a second average amplitude. The third section may have a third average amplitude. The fourth section may have a fourth average amplitude, and so forth. The method 500 may include calculating a difference between: the first average amplitude and the second average amplitude; the first average amplitude and the third average amplitude; the first average amplitude and the fourth average amplitude; the second average amplitude and the third average amplitude; and so forth (block 510). The difference may correspond to a change in an amount of a constituent of the subject's blood. The method 500 may include using the difference to determine the change in the amount of constituent (block 512). This may include comparing the difference to a table or calculating the change based on a formula. For example, the constituent may be glucose. The formula may state that a change of X microvolts in amplitude corresponds with a change of Y milligrams per deciliter of blood glucose.

An implementation of the method 500 may be executed by a system that includes a first sensor, a second sensor, a processing device, and a memory device. The first and second sensors may be configured to measure a first physiological parameter of a subject. The processing device may be communicatively coupled to the first sensor and/or the second sensor. The memory device may be communicatively coupled to the processing device. The memory device may store instructions associated with the method 500 that are executable by the processing device.

In a specific implementation, the method 500 may be executed on and/or by a wearable device. The wearable device may include a light source configured to emit light that is absorbed by blood glucose. The light source may be positioned in or on the wearable device to emit the light towards a body part of a subject as the subject wears the wearable device. The wearable device may include an optical sensor configured to detect the light. The optical sensor may be positioned in or on the wearable device to detect reflected light passing through a vein or an artery of the subject. The wearable device may include an impedance sensor configured to detect an impedance signal corresponding to an impedance of blood in the vein or the artery. The impedance sensor may be positioned in or on the wearable device adjacent to the optical sensor or the light source. The wearable device may include a processing device coupled to the light source, the optical sensor, and/or the impedance sensor. The wearable device may include a memory device coupled to the processing device. The memory device may store instructions associated with various elements of the method 500 that are executable by the processing device.

In various implementations, instructions associated with the method 500 may be executable by a processing device to determine first signal data based on a first signal output by the first sensor during a measurement period. The measurement period may be based on a variation rate of the physiological parameter or an input received by and/or from a user device. The first signal data may indicate a first set of parameter measurements corresponding to the first physiological parameter. The first signal data may indicate first noise that obscures the first set of parameter measurements. The first physiological parameter may, for example, be blood glucose, hematocrit, a hormone, blood oxygen, blood alcohol, plasma, water, and so forth. In a specific implementation, the instructions may be executable to determine, for a set of optical measurements taken during a measurement period, optical data based on the reflected light that is detected by the optical sensor. The optical data may indicate a first set of blood glucose measurements and optical noise that obscures the first set of blood glucose measurements. The optical data may be based on a voltage output by the optical sensor.

The instructions may be executable to determine second signal data based on a second signal output by the second sensor during the measurement period. The second sensor may be a type of sensor that is different from the first sensor. The type may, for example, be an optical sensor, an impedance sensor, an optical spectrometer, or an impedance spectrometer. The second signal data may indicate a second set of parameter measurements corresponding to the first physiological parameter. The second signal data may indicate second noise that obscures the second measurement data. The second noise may be non-correlative with the first noise. In a specific implementation, the instructions may be executable to determine, for a set of impedance measurements taken during the measurement period, impedance data based on the impedance signal detected by the impedance sensor. The impedance data may indicate a second set of blood glucose measurements and impedance noise that obscures the second set of blood glucose measurements. The impedance noise may be non-correlative with the optical noise. The impedance data may be based on a voltage output by the impedance sensor.

The instructions may be executable to generate, by a correlation function, combined data based on the first signal data and the second signal data. The combined data may indicate combined noise that is dampened relative to the first noise and the second noise. The combined data may indicate a set of combined measurements that are more clearly indicative of the physiological parameter of interest. To generate the combined data by the correlation function, the instructions may be executable to normalize the first signal data and the second signal data to a uniform scale. For example, the first signal data may have a range of variation that is significantly greater than the range of variation of the second signal data. The first signal data may indicate voltages that, on average, are notably higher than the voltages indicated by the second signal data.

In a specific implementation, the instructions may be executable to generate, by the correlation function, combined data based on the optical data and the impedance data. The correlation function may be a function of amplitude and time. The combined data may indicate combined noise that is dampened relative to the optical noise and the impedance noise. The combined data may indicate a set of combined blood glucose measurements that more clearly indicate the blood glucose level of the subject.

The instructions may be executable to determine first average amplitude data for a first time segment of the combined data. The instructions may be executable to determine second average amplitude data for a second time segment of the combined data. The second time segment may be immediately after the first time segment. A third time segment may be between the first time segment and the second time segment. The instructions may be executable to determine, based on the first average amplitude data and the second average amplitude data, change data that indicates a change in the first physiological parameter. In a specific implementation, the instructions may be executable to determine, based on the first average amplitude data and the second average amplitude data, change data that indicates a change in the blood glucose level of the subject.

The instructions may be executable to output the change data to the memory device or another device in communication with the processing device. The system may further include a display device coupled to the processing device or the memory device. The instructions may be executable to generate display data based on the change data and output the display data to the display device. The system may include a communication device coupled to the processing device or the memory device. The instructions may be executable to output the change data to a server device and/or user device via the communication device.

The first sensor and/or the second sensor may be configured to measure a second physiological parameter that has a different variation rate than the first physiological parameter. For example, the first sensor and/or the second sensor may be a spectrometer. In a specific implementation, optical data output by an optical sensor, or impedance data output by an impedance sensor, may include spectral data. The spectral data may indicate multiple (e.g., two or more) frequency domains corresponding, respectively, to multiple physiological parameters of the subject.

In various implementations, the first sensor may be a first portion of a spectrometer that detects spectra within a first range. The second sensor may be a second portion of the spectrometer that detects spectra within a second range. As a specific example, the spectrometer may be an optical sensor with multiple pixels. A first pixel, or first set of pixels, may detect light having a first range of wavelengths, and a second pixel, or second set of pixels, may detect light having a second range of wavelengths. The first range of wavelengths and the second range of wavelengths may correspond to a physiological parameter such as blood glucose. The first range of wavelengths may further be indicative of a second physiological parameter that is not indicated by the second range of wavelengths. The second range of wavelengths may be indicative of a third physiological parameter that is not indicated by the first range of wavelengths. Measurement data from the first pixel and the second pixel may be correlated to eliminate or minimize the portions of the measurement data attributable to the second and third physiological parameters. Measurement data corresponding to the first physiological parameter may be amplified and/or maintained.

The first set of parameter measurements and the second set of parameter measurements may be indicative of a second physiological parameter. Combined data generated based on the two sets may indicate a set of combined measurements corresponding to the second physiological parameter. The instructions may be executable to differentiate between the first physiological parameter and the second physiological parameter based on a time domain relative to each parameter. The time domain may be indicative of a change in one parameter and not sufficiently long or too long to be indicative of the other parameter.

Figure 6:
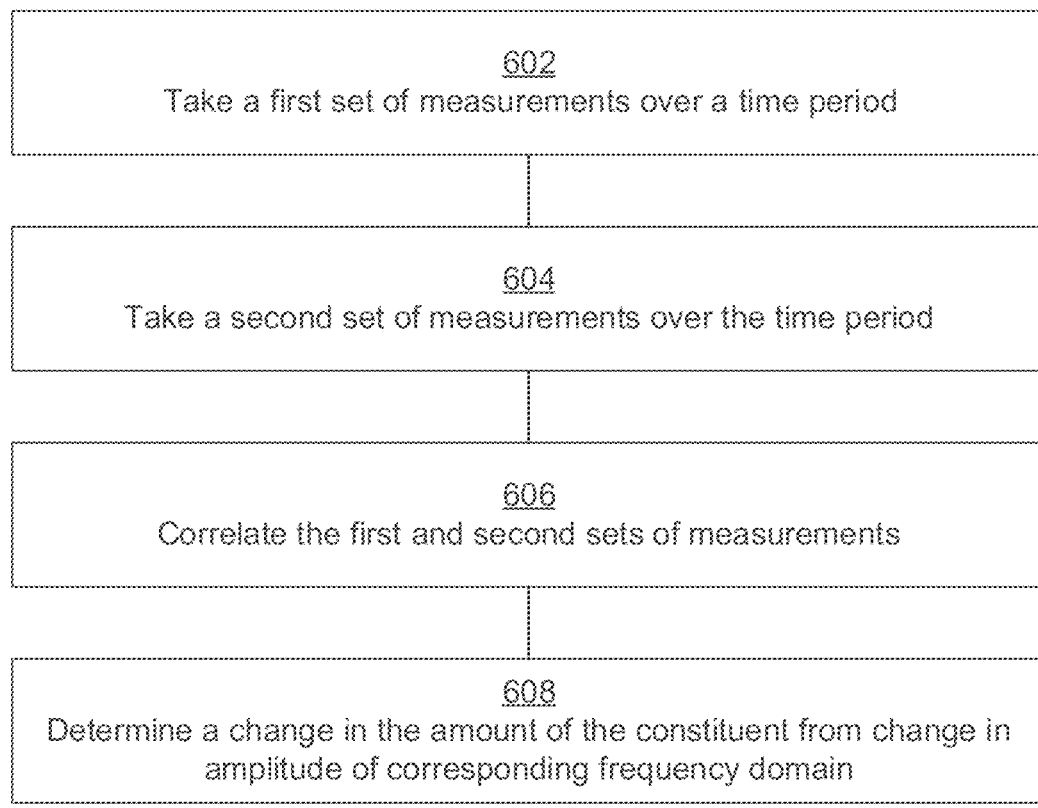
FIG. 6 illustrates a second method of determining a change in a constituent of interest using two correlated measurement signals, according to an embodiment.

FIG. 6 illustrates a second method 600 of determining a change in a constituent of interest using two correlated measurement signals, according to an embodiment. Some of the features in FIG. 6 may be the same as or similar to some of the features in the other FIGs. described herein as noted by same and/or similar reference characters, unless expressly described otherwise. Additionally, reference may be made to features shown in any of the other FIGs. described herein and not shown in FIG. 6.

The method 600 may include taking a first set of measurements over a time period by an optical sensor (block 602). The first set of measurements may be embodied in an electronic signal. The electronic signal may include a set of frequency domains optically tuned to measure separate blood constituents. The method 600 may include taking a second set of measurements over the time period by a second sensor (block 604). The method 600 may include removing noise from the first set of measurements and/or the second set of measurements by correlating the first set of measurements with the second set of measurements (block 606). The method 600 may include determining a change in a blood constituent of interest from a change in amplitude of the electronic signal for the frequency domain corresponding to the constituent of interest (block 608).

Figure 7:
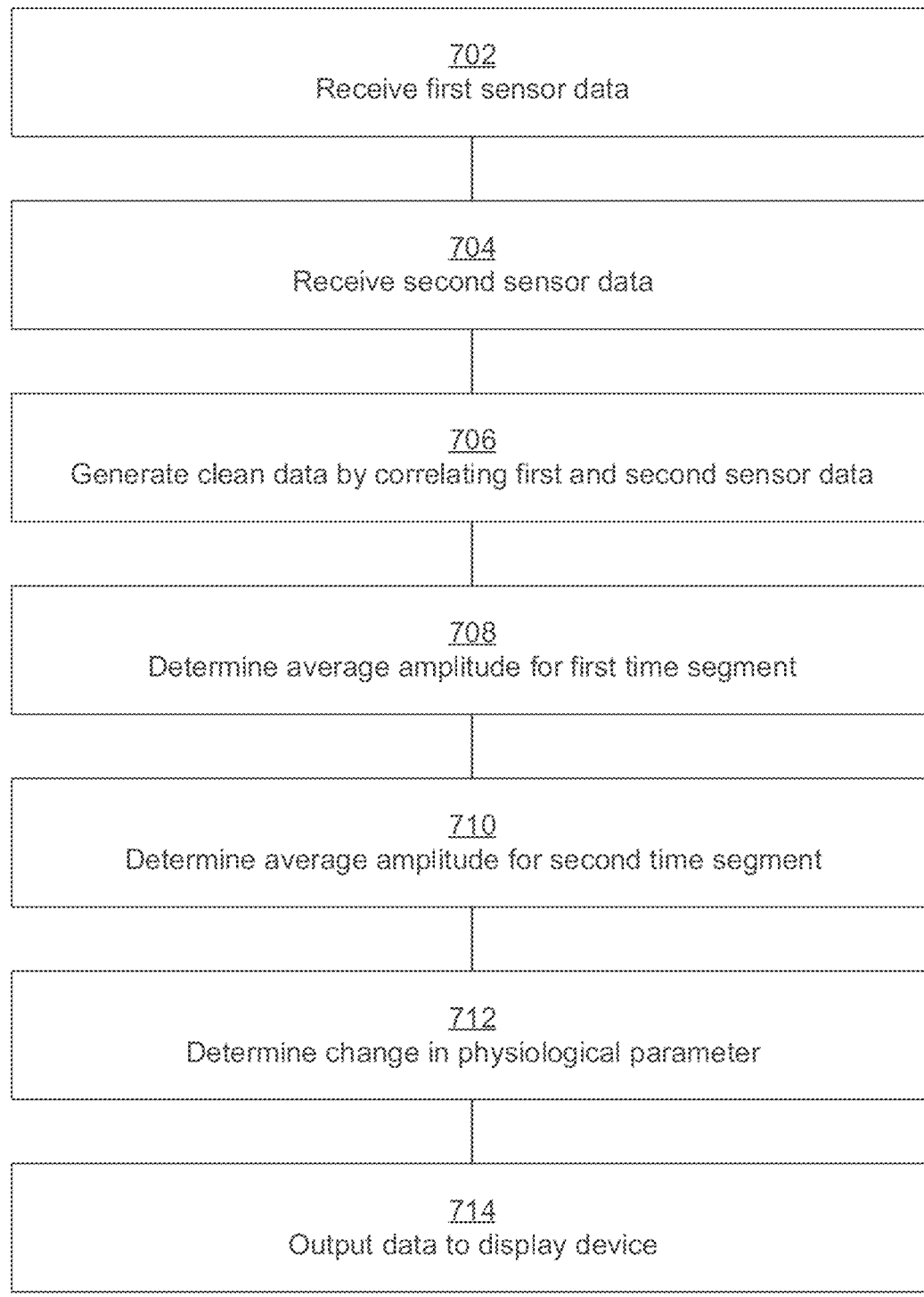
FIG. 7 illustrates a method of determining a change in a physiological parameter of a subject by correlating sensor measurements from different kinds of sensors, according to an embodiment.

FIG. 7 illustrates a method 700 of determining a change in a physiological parameter of a subject by correlating sensor measurements from different kinds of sensors, according to an embodiment. By correlating sensor measurements, noise is eliminated from data. This allows for more precise measurement of various physiological parameters using non-invasive means. Some of the features in FIG. 7 may be the same as or similar to some of the features in the other FIGs. described herein as noted by same and/or similar reference characters, unless expressly described otherwise. Additionally, reference may be made to features shown in any of the other FIGs. described herein and not shown in FIG. 7.

The method 700 may include receiving first sensor data based on an output of a first physiological sensor during a measurement period (block 702). The first sensor data may include a first noise component and a first measurement component. The first sensor data may be received by a processing device. The processing device may be a component of a medical device, a wearable health monitor, a smartwatch, a smartphone, a personal computer, and/or a cloud-based data processing system. The method 700 may include receiving, by the processing device, second sensor data based on an output of a second physiological sensor during the measurement period (block 704). The second sensor data may include a second noise component and a second measurement component.

The first physiological sensor may measure the first physiological parameter by a different physical mechanism than the second physiological sensor. Accordingly, the second sensor data may be independent of the first sensor data. The first noise component or the second noise component may be indicative of electronic noise generated by the first physiological sensor and/or the second physiological sensor, a heartbeat waveform of the subject, or another physiological parameter. The first measurement component and/or the second measurement component may be indicative of the same physiological parameter of the subject.

The method 700 may include generating, by the processing device, clean data based on a correlation of the first sensor data and the second sensor data (block 706). The clean data may include a dampened noise component that is dampened relative to the first noise component and the second noise component. The clean data may include a clean measurement component from which the physiological parameter is more clearly discernable relative to the first measurement component and the second measurement component.

The method 700 may include determining, by the processing device, first average amplitude data for a first time segment of the clean data (block 708). The method 700 may include determining, by the processing device, second average amplitude data for a second time segment of the clean data (block 710). The method 700 may include determining, by the processing device, and based on the first average amplitude data and the second average amplitude data, change data that indicates a change in a physiological parameter of the subject (block 712). A measurement of a second physiological parameter may be determined based on the first sensor data or the second sensor data. The other sensor data may not be indicative of the measurement of the other physiological parameter. For example, the first sensor data may include a first frequency domain that is indicative of the first physiological parameter and a second frequency domain that is indicative of the other physiological parameter. The method 700 may include outputting the change data to a device configured to store and/or display the change data (block 714)

Figure 8:
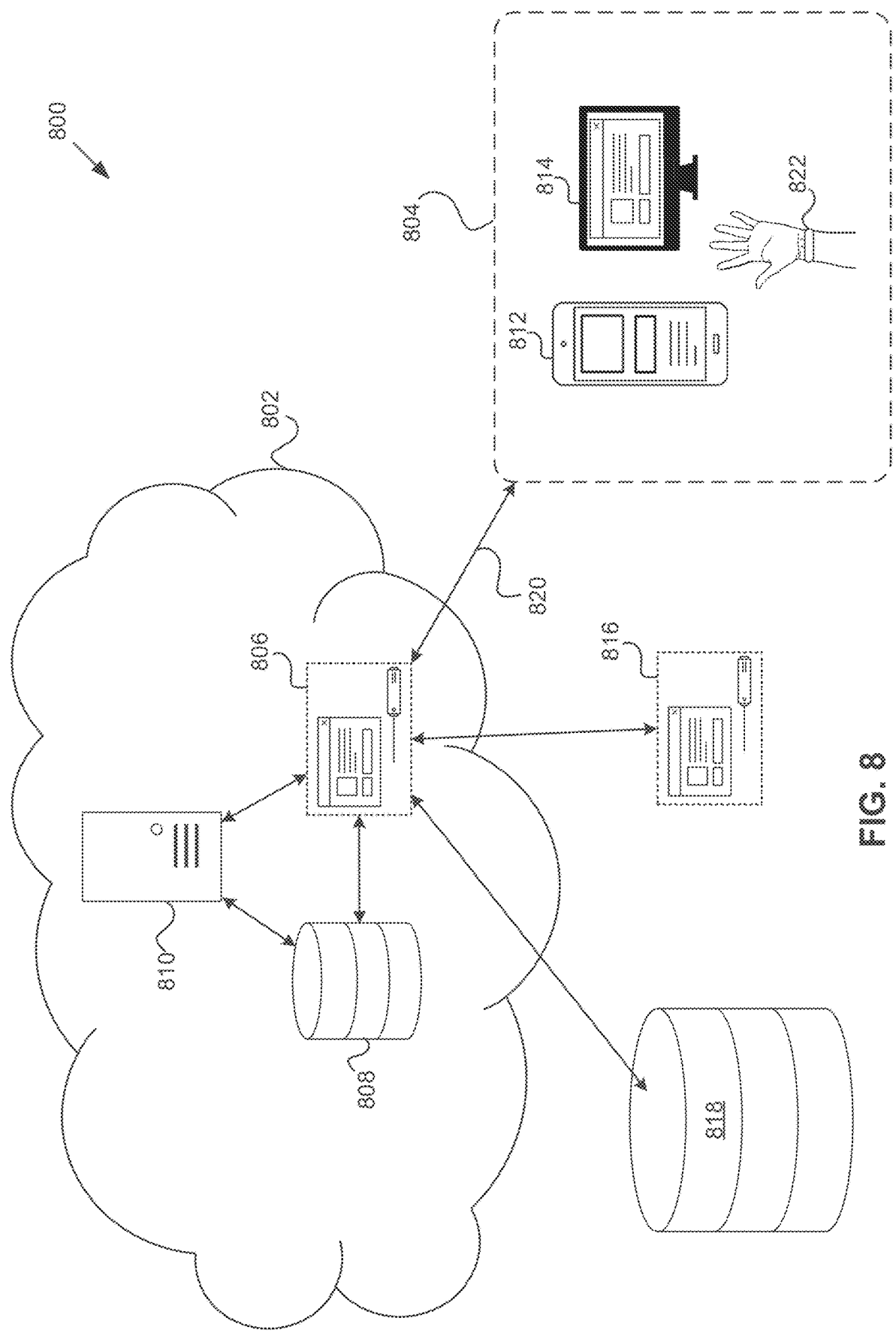
FIG. 8 illustrates a measurement processing system, according to an embodiment.

FIG. 8 illustrates a measurement processing system 800, according to an embodiment. The measurement processing system 800 may enable remote monitoring of a patient's health condition. The measurement processing system 800 may further enable noise-elimination from sensor data to obtain more precise measurements of various physiological parameters. The sensors may take such measurements non-invasively, which prevents injury to subjects and eliminates the risk of infection. Some of the features in FIG. 8 may be the same as or similar to some of the features in the other FIGs. described herein as noted by same and/or similar reference characters, unless expressly described otherwise. Additionally, reference may be made to features shown in any of the other FIGs. described herein and not shown in FIG. 8.

The measurement processing system 800 may include a cloud-based data management system 802 and a user device 804. The cloud-based data management system 802 may include an application server 806, a database 808, and a data server 810. The user device 804 may include one or more devices associated with user profiles of the measurement processing system 800, such as a smartphone 812, a personal computer 814, and/or a wearable device 822. The wearable device may include various sensors for measuring physiological parameters of a subject. The measurement processing system 800 may include external resources such as an external application server 816 and/or an external database 818. The various elements of the measurement processing system 800 may communicate via various communication links 820. An external resource may generally be considered a data resource owned and/or operated by an entity other than an entity that utilizes the cloud-based data management system 802 and/or the user device 804.

The communication links 820 may be direct or indirect. A direct link may include a link between two devices where information is communicated from one device to the other without passing through an intermediary. For example, the direct link may include a Bluetooth™ connection, a Zigbee® connection, a Wifi Direct™ connection, a near-field communications (NFC) connection, an infrared connection, a wired universal serial bus (USB) connection, an ethernet cable connection, a fiber-optic connection, a firewire connection, a microwire connection, and so forth. In another example, the direct link may include a cable on a bus network. "Direct," when used regarding the communication links 820, may refer to any of the aforementioned direct communication links.

An indirect link may include a link between two or more devices where data may pass through an intermediary, such as a router, before being received by an intended recipient of the data. For example, the indirect link may include a wireless fidelity (WiFi) connection where data is passed through a WiFi router, a cellular network connection where data is passed through a cellular network router, a wired network connection where devices are interconnected through hubs and/or routers, and so forth. The cellular network connection may be implemented according to one or more cellular network standards, including the global system for mobile communications (GSM) standard, a code division multiple access (CDMA) standard such as the universal mobile telecommunications standard, an orthogonal frequency division multiple access (OFDMA) standard such as the long term evolution (LTE) standard, and so forth. "Indirect," when used regarding the communication links 820, may refer to any of the aforementioned indirect communication links.

Figure 9:
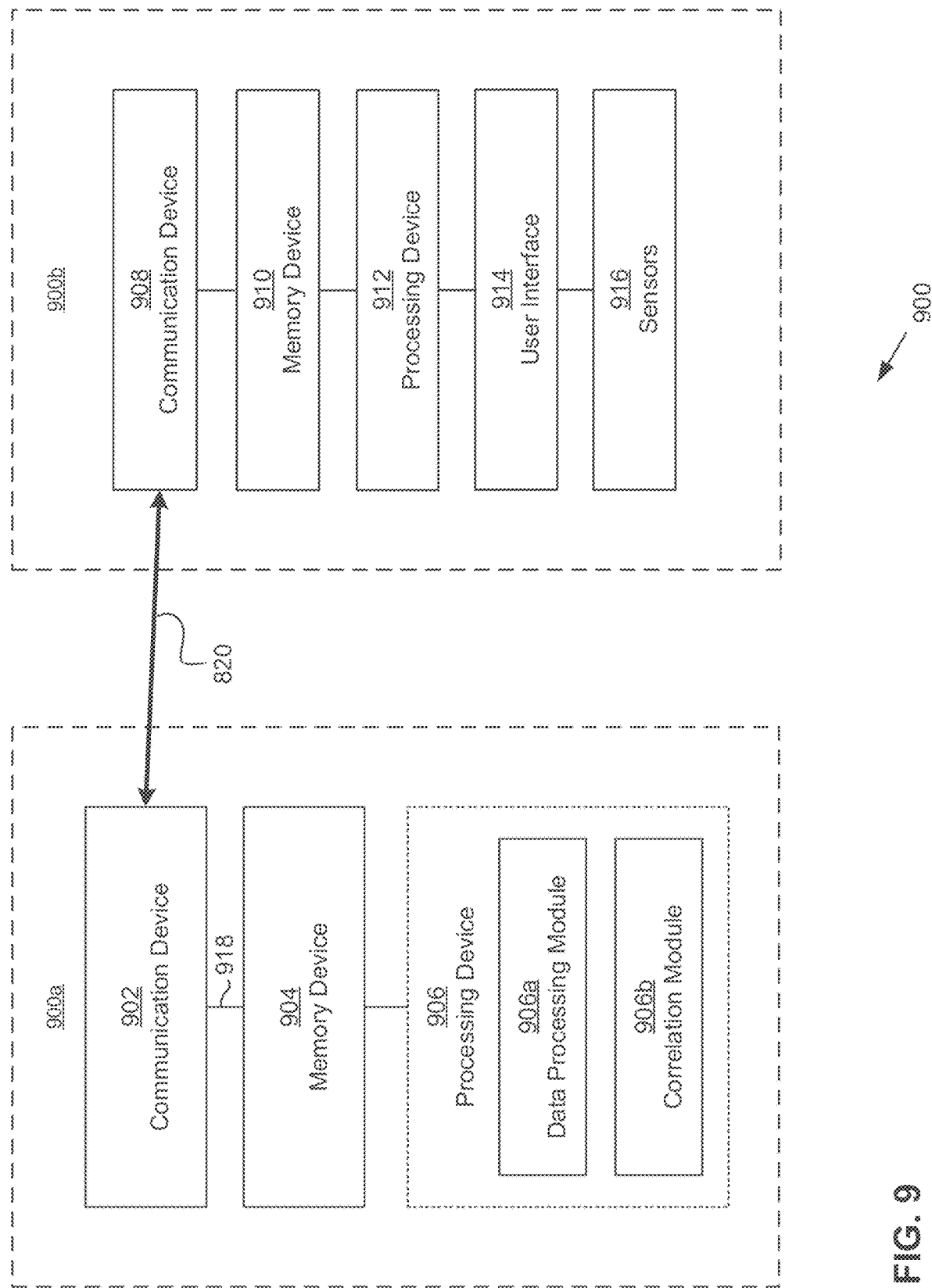
FIG. 9 illustrates a device schematic for various devices used in the measurement processing system, according to an embodiment.

FIG. 9 illustrates a device schematic 900 for various devices used in the measurement processing system 800, according to an embodiment. A server device 900a may moderate data communicated to a client device 900b based on data permissions to minimize memory resource allocation at the client device 900b. Some of the features in FIG. 9 may be the same as or similar to some of the features in the other FIGs. described herein as noted by same and/or similar reference characters, unless expressly described otherwise. Additionally, reference may be made to features shown in any of the other FIGs. described herein and not shown in FIG. 9.

The server device 900a may include a communication device 902, a memory device 904, and a processing device 906. The processing device 906 may include a data processing module 906a and a correlation module 906b, where module refers to specific programming that governs how data is handled by the processing device 906. The client device 900b may include a communication device 908, a memory device 910, a processing device 912, a user interface 914, and/or sensors 916. Various hardware elements within the server device 900a and/or the client device 900b may be interconnected via a system bus 918. The system bus 918 may be and/or include a control bus, a data bus, an address bus, and so forth. The communication device 902 of the server device 900a may communicate with the communication device 908 of the client device 900b.

The data processing module 906a may handle inputs from the client device 900b. The data processing module 906a may cause data to be written and stored in the memory device 904 based on the inputs from the client device 900b. The data processing module 906a may retrieve data stored in the memory device 904 and output the data to the client device 900b via the communication device 902. The correlation module 906b may determine, based on sensor data received at the server device 900a, cleaned-up data that has dampened noise and clear measurements. In various implementations, the processing device 912 of the client device 900b may include a correlation module that cleans up sensor data directly at the client device 900b.

The server device 900a may be representative of the cloud-based data management system 802. The server device 900a may be representative of the application server 806. The server device 900a may be representative of the data server 810. The server device 900a may be representative of the external application server 816. The memory device 904 may be representative of the database 808 and the processing device 906 may be representative of the data server 810. The memory device 904 may be representative of the external database 818 and the processing device 906 may be representative of the external application server 816. For example, the database 808 and/or the external database 818 may be implemented as a block of memory in the memory device 904. The memory device 904 may further store instructions that, when executed by the processing device 906, perform various functions with the data stored in the database 808 and/or the external database 818.

Similarly, the client device 900b may be representative of the user device 804. The client device 900b may be representative of the smartphone 812. The client device 900b may be representative of the personal computer 814. The client device 900b may be representative of the wearable device 822. The memory device 910 may store application instructions that, when executed by the processing device 912, cause the client device 900b to perform various functions associated with the instructions, such as retrieving data, processing data, receiving sensor data, processing sensor data, receiving input, processing input, transmitting data, and so forth.

As stated above, the server device 900a and the client device 900b may be representative of various devices of the measurement processing system 800. Various of the elements of the measurement processing system 800 may include data storage and/or processing capabilities. Such capabilities may be rendered by various electronics for processing and/or storing electronic signals. One or more of the devices in the measurement processing system 800 may include a processing device. For example, the cloud-based data management system 802, the user device 804, the smartphone 812, the personal computer 814, the wearable device 822, the external application server 816, and/or the external database 818 may include a processing device. One or more of the devices in the measurement processing system 800 may include a memory device. For example, the cloud-based data management system 802, the user device 804, the smartphone 812, the personal computer 814, the wearable device 822, the external application server 816, and/or the external database 818 may include the memory device.

The processing device may have volatile and/or persistent memory. The memory device may have volatile and/or persistent memory. The processing device may have volatile memory and the memory device may have persistent memory. The processing device may generate an output based on an input. For example, the processing device may receive an electronic and/or digital signal. The processing device may read the signal and perform one or more tasks with the signal, such as performing various functions with data in response to input received by the processing device. The processing device may read from the memory device information needed to perform the functions. The processing device may send an output signal to the memory device, and the memory device may store data according to the signal output by the processing device.

The processing device may be and/or include a processor, a microprocessor, a computer processing unit (CPU), a graphics processing unit (GPU), a neural processing unit, a physics processing unit, a digital signal processor, an image signal processor, a synergistic processing element, a field-programmable gate array (FPGA), a sound chip, a multi-core processor, and so forth. As used herein, "processor," "processing component," "processing device," and/or "processing unit" may be used generically to refer to any or all of the aforementioned specific devices, elements, and/or features of the processing device.

The memory device may be and/or include a computer processing unit register, a cache memory, a magnetic disk, an optical disk, a solid-state drive, and so forth. The memory device may be configured with random access memory (RAM), read-only memory (ROM), static RAM, dynamic RAM, masked ROM, programmable ROM, erasable and programmable ROM, electrically erasable and programmable ROM, and so forth. As used herein, "memory," "memory component," "memory device," and/or "memory unit" may be used generically to refer to any or all of the aforementioned specific devices, elements, and/or features of the memory device.

Various of the devices in the measurement processing system 800 may include data communication capabilities. Such capabilities may be rendered by various electronics for transmitting and/or receiving electronic and/or electromagnetic signals. One or more of the devices in the measurement processing system 800 may include a communication device, e.g., the communication device 902 and/or the communication device 908. For example, the cloud-based data management system 802, the user device 804, the smartphone 812, the personal computer 814, the application server 816, the wearable device 822, and/or the external database 818 may include a communication device.

The communication device may include, for example, a networking chip, one or more antennas, and/or one or more communication ports. The communication device may generate radio frequency (RF) signals and transmit the RF signals via one or more of the antennas. The communication device may receive and/or translate the RF signals. The communication device may transceive the RF signals. The RF signals may be broadcast and/or received by the antennas.

The communication device may generate electronic signals and transmit the RF signals via one or more of the communication ports. The communication device may receive the RF signals from one or more of the communication ports. The electronic signals may be transmitted to and/or from a communication hardline by the communication ports. The communication device may generate optical signals and transmit the optical signals to one or more of the communication ports. The communication device may receive the optical signals and/or may generate one or more digital signals based on the optical signals. The optical signals may be transmitted to and/or received from a communication hardline by the communication port, and/or the optical signals may be transmitted and/or received across open space by the networking device.

The communication device may include hardware and/or software for generating and communicating signals over a direct and/or indirect network communication link. For example, the communication component may include a USB port and a USB wire, and/or an RF antenna with Bluetooth™ programming installed on a processor, such as the processing component, coupled to the antenna. In another example, the communication component may include an RF antenna and programming installed on a processor, such as the processing device, for communicating over a Wifi and/or cellular network. As used herein, "communication device" "communication component," and/or "communication unit" may be used generically herein to refer to any or all of the aforementioned elements and/or features of the communication component.

Various of the elements in the measurement processing system 800 may be referred to as a "server." Such elements may include a server device. The server device may include a physical server and/or a virtual server. For example, the server device may include one or more bare-metal servers. The bare-metal servers may be single-tenant servers or multiple tenant servers. In another example, the server device may include a bare metal server partitioned into two or more virtual servers. The virtual servers may include separate operating systems and/or applications from each other. In yet another example, the server device may include a virtual server distributed on a cluster of networked physical servers. The virtual servers may include an operating system and/or one or more applications installed on the virtual server and distributed across the cluster of networked physical servers. In yet another example, the server device may include more than one virtual server distributed across a cluster of networked physical servers.

The term server may refer to functionality of a device and/or an application operating on a device. For example, an application server may be programming instantiated in an operating system installed on a memory device and run by a processing device. The application server may include instructions for receiving, retrieving, storing, outputting, and/or processing data. A processing server may be programming instantiated in an operating system that receives data, applies rules to data, makes inferences about the data, and so forth. Servers referred to separately herein, such as an application server, a processing server, a collaboration server, a scheduling server, and so forth may be instantiated in the same operating system and/or on the same server device. Separate servers may be instantiated in the same application or in different applications.

Various aspects of the systems described herein may be referred to as "data." Data may be used to refer generically to modes of storing and/or conveying information. Accordingly, data may refer to textual entries in a table of a database. Data may refer to alphanumeric characters stored in a database. Data may refer to machine-readable code. Data may refer to images. Data may refer to audio. Data may refer to, more broadly, a sequence of one or more symbols. The symbols may be binary. Data may refer to a machine state that is computer-readable. Data may refer to human-readable text.

Various of the devices in the measurement processing system 800, including the server device 900a and/or the client device 900b, may include a user interface for outputting information in a format perceptible by a user and receiving input from the user, e.g., the user interface 914. The user interface may include a display screen such as a light-emitting diode (LED) display, an organic LED (OLED) display, an active-matrix OLED (AMOLED) display, a liquid crystal display (LCD), a thin-film transistor (TFT) LCD, a plasma display, a quantum dot (QLED) display, and so forth. The user interface may include an acoustic element such as a speaker, a microphone, and so forth. The user interface may include a button, a switch, a keyboard, a touch-sensitive surface, a touchscreen, a camera, a fingerprint scanner, and so forth. The touchscreen may include a resistive touchscreen, a capacitive touchscreen, and so forth.

The above description sets forth numerous specific details such as examples of specific systems, components, methods and so forth, to provide a good understanding of several implementations. It will be apparent to one skilled in the art, however, that at least some implementations may be practiced without these specific details. In other instances, well-known components or methods are not described in detail or are presented in simple block diagram format to avoid unnecessarily obscuring the present implementations. Thus, the specific details set forth above are merely exemplary. Particular implementations may vary from these exemplary details and still be contemplated to be within the scope of the present implementations.

It is to be understood that the above description is intended to be illustrative and not restrictive. Many other implementations will be apparent to those of skill in the art upon reading and understanding the above description. The scope of the present implementations should, therefore, be determined regarding the appended claims, if any, along with the full scope of equivalents to which such claims are entitled.

The disclosure above encompasses multiple distinct embodiments with independent utility. While these embodiments have been disclosed in a particular form, the specific embodiments disclosed and illustrated above are not to be considered in a limiting sense as numerous variations are possible. The subject matter of the embodiments includes the novel and non-obvious combinations and sub-combinations of the various elements, features, functions and/or properties disclosed above and inherent to those skilled in the art regarding such embodiments. Where the disclosure or subsequently filed claims recite "a" element, "a first" element, or any such equivalent term, the disclosure or claims is to be understood to incorporate one or more such elements, neither requiring nor excluding two or more of such elements.

The Applicant(s) reserves the right to submit other claims than those provided below. Such other claims may be directed to combinations and sub-combinations of the disclosed embodiments that are believed to be novel and non-obvious. Embodiments embodied in other combinations and sub-combinations of features, functions, elements, and/or properties may be claimed through amendment of those claims or presentation of new claims in the present application or in a related application. Such amended or new claims, whether they are directed to the same embodiment or a different embodiment and whether they are different, broader, narrower, or equal in scope to the original claims, are to be considered within the subject matter of the embodiments described herein.

The invention claimed is:

1. A wearable device, comprising:
   a light source configured to emit light that is absorbed by blood glucose, the light source positioned on the wearable device to emit the light towards a body part of a subject as the subject wears the wearable device;
   an optical sensor configured to detect the light and positioned on the wearable device to detect reflected light passing through a vein or an artery of the subject;
   an impedance sensor configured to detect an impedance signal corresponding to an impedance of blood in the vein or the artery, the impedance sensor positioned in the wearable device adjacent to the optical sensor or the light source;
   a processing device coupled to the light source, the optical sensor, and the impedance sensor; and
   a memory device coupled to the processing device, the memory device storing instructions executable by the processing device to:
      determine, for a set of optical measurements taken during a measurement period, optical data based on the reflected light that is detected by the optical sensor, wherein the optical data indicates:
         a first set of blood glucose measurements; and
         optical noise that obscures the first set of blood glucose measurements;
      determine, for a set of impedance measurements taken during the measurement period, impedance data based on the impedance signal detected by the impedance sensor, wherein the impedance data indicates:
         a second set of blood glucose measurements; and
         impedance noise that obscures the second set of blood glucose measurements, wherein the impedance noise is non-correlative with the optical noise;
      generate, by a correlation function, combined data based on the optical data and the impedance data, wherein:
         the correlation function is a function of amplitude and time;
         the combined data indicates combined noise that is dampened relative to the optical noise and the impedance noise; and
         the combined data indicates a set of combined blood glucose measurements that are amplified or maintained relative to the first set of blood glucose measurements and the second set of blood glucose measurements;
      determine first average amplitude data for a first time segment of the combined data;
      determine second average amplitude data for a second time segment of the combined data;
      determine, based on the first average amplitude data and the second average amplitude data, change data that indicates a change in a blood glucose level of the subject; and
      output the change data to the memory device or another device in communication with the processing device.

2. The wearable device of claim 1, wherein:
   the optical data is further based on a voltage output by the optical sensor; and
   the impedance data is further based on a voltage output by the impedance sensor.

3. The wearable device of claim 1, wherein, to generate the combined data by the correlation function, the instructions are further executable to normalize the optical data and the impedance data to a uniform scale.

4. The wearable device of claim 1, wherein:
   the second time segment is immediately after the first time segment; or
   a third time segment is between the first time segment and the second time segment.

5. The wearable device of claim 1, further comprising a display device coupled to the processing device or the memory device, and the instructions further executable to:
   generate display data based on the change data; and
   output the display data to the display device.

6. The wearable device of claim 1, further comprising a communication device coupled to the processing device or the memory device, the instructions further executable to output the change data to a server device via the communication device.

7. The wearable device of claim 1, wherein the optical data or the impedance data comprises spectral data that indicates multiple frequency domains corresponding, respectively, to multiple blood constituents of the subject.

8. A system, comprising:
   a first sensor configured to measure a first physiological parameter of a subject;
   a second sensor configured to measure the first physiological parameter;
   a processing device communicatively coupled to the first sensor and the second sensor; and
   a memory device communicatively coupled to the processing device, the memory device storing instructions executable by the processing device to:
      determine first signal data based on a first signal output by the first sensor during a measurement period, wherein the first signal data indicates:
         a first set of parameter measurements corresponding to the first physiological parameter; and
         first noise that obscures the first set of parameter measurements;

determine second signal data based on a second signal output by the second sensor during the measurement period, wherein the second signal data indicates:
   a second set of parameter measurements corresponding to the first physiological parameter; and
   second noise that obscures the second measurement data, wherein the second noise is non-correlative with the first noise;
generate, by a correlation function, combined data based on the first signal data and the second signal data, wherein the combined data indicates:
   combined noise that is dampened relative to the first noise and the second noise; and
   a set of combined measurements that are amplified or maintained relative to the first set of parameter measurements and the second set of parameter measurements;
determine first average amplitude data for a first time segment of the combined data;
determine second average amplitude data for a second time segment of the combined data;
determine, based on the first average amplitude data and the second average amplitude data, change data that indicates a change in the first physiological parameter; and
output the change data to the memory device or another device in communication with the processing device.

9. The system of claim 8, wherein the first physiological parameter comprises blood glucose, hematocrit, a hormone, blood oxygen, blood alcohol, plasma, or water.

10. The system of claim 8, wherein:
   the first sensor is a first portion of a spectrometer corresponding to a first spectral range; and
   the second sensor is a second portion of the spectrometer corresponding to a second spectral range.

11. The system of claim 8, wherein:
   the first sensor and the second sensor are configured to measure a second physiological parameter that has a different variation rate than the first physiological parameter;
   the first set of parameter measurements and the second set of parameter measurements are indicative of the second physiological parameter;
   the combined data indicates a second set of combined measurements corresponding to the second physiological parameter; and
   the instructions are further executable to determine the first time segment and the second time segment such that the change data is indicative of the first physiological parameter and not the second physiological parameter.

12. The system of claim 8, wherein the first sensor and the second sensor are integrated into a wrist-worn device.

13. The system of claim 12, wherein the processing device or the memory device is:
   a component of a cloud-based data analytics system communicatively coupled to the wrist-worn device; or
   a component of a smartphone communicatively coupled to the wrist-worn device.

14. The system of claim 8, wherein the instructions are further executable to determine the measurement period based on:
   a variation rate of the physiological parameter; or
   an input received from a user device.

15. A method, comprising:
receiving, by a processing device, first sensor data based on an output of a first physiological sensor during a measurement period, wherein the first sensor data comprises a first noise component and a first measurement component;
receiving, by the processing device, second sensor data based on an output of a second physiological sensor during the measurement period, wherein the second sensor data comprises a second noise component and a second measurement component;
generating, by the processing device, clean data based on a correlation of the first sensor data and the second sensor data, wherein the clean data comprises:
   a dampened noise component that is dampened relative to the first noise component and the second noise component; and
   a combined measurement component that is indicative of the physiological parameter;
determining, by the processing device, first average amplitude data for a first time segment of the clean data;
determining, by the processing device, second average amplitude data for a second time segment of the clean data;
determining, by the processing device based on the first average amplitude data and the second average amplitude data, change data that indicates a change in a first physiological parameter; and
outputting the change data to a device configured to store or display the change data.

16. The method of claim 15, wherein the processing device is a component of:
   a medical device;
   a wearable health monitor;
   a smartwatch;
   a smartphone;
   a personal computer; or
   a cloud-based data processing system.

17. The method of claim 15, wherein the first physiological sensor measures the first physiological parameter by a different physical mechanism than the second physiological sensor.

18. The method of claim 15, further comprising determining a measurement of a second physiological parameter based on the first sensor data, wherein the second sensor data is not indicative of the measurement of the second physiological parameter.

19. The method of claim 18, wherein the first sensor data comprises:
   a first frequency domain that is indicative of the first physiological parameter; and
   a second frequency domain that is indicative of the second physiological parameter.

20. The method of claim 15, wherein the first noise component or the second noise component is indicative of:
   electronic noise generated by the first physiological sensor or the second physiological sensor; or
   a heartbeat waveform.

* * * * *